(12) United States Patent
Kitamoto

(10) Patent No.: US 8,901,171 B2
(45) Date of Patent: Dec. 2, 2014

(54) COMPOUNDS FOR SUPPRESSING A PERIPHERAL NERVE DISORDER INDUCED BY AN ANTI-CANCER AGENT

(71) Applicant: Takeda Pharmaceutical Company Limited, Osaka (JP)

(72) Inventor: Naomi Kitamoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/971,159

(22) Filed: Aug. 20, 2013

(65) Prior Publication Data

US 2013/0345304 A1    Dec. 26, 2013

Related U.S. Application Data

(63) Continuation of application No. 13/574,848, filed as application No. PCT/JP2011/052077 on Jan. 26, 2011.

(30) Foreign Application Priority Data

Jan. 27, 2010   (JP) .................................. 2010-015935

(51) Int. Cl.
| | | |
|---|---|---|
| C07C 311/28 | (2006.01) | |
| A61K 31/69 | (2006.01) | |
| A61K 31/4545 | (2006.01) | |
| A61K 31/428 | (2006.01) | |
| A61K 31/4192 | (2006.01) | |
| A61K 31/282 | (2006.01) | |
| A61K 31/337 | (2006.01) | |
| A61K 31/4196 | (2006.01) | |
| A61K 31/41 | (2006.01) | |
| A61K 31/216 | (2006.01) | |

(52) U.S. Cl.
CPC ............... *C07C 311/28* (2013.01); *A61K 31/69* (2013.01); *A61K 31/4545* (2013.01); *A61K 31/428* (2013.01); *A61K 31/4192* (2013.01); *A61K 31/282* (2013.01); *A61K 31/337* (2013.01); *A61K 31/4196* (2013.01); *A61K 31/41* (2013.01); *A61K 31/216* (2013.01)
USPC .......................................................... 514/529

(58) Field of Classification Search
USPC .......................................................... 514/529
See application file for complete search history.

(56) References Cited

U.S. PATENT DOCUMENTS

| | | | |
|---|---|---|---|
| 4,769,372 A | 9/1988 | Kreek | |
| 4,785,000 A | 11/1988 | Kreek et al. | |
| 5,053,419 A | 10/1991 | Lipton | |
| 5,059,712 A | 10/1991 | Griffith | |
| 5,158,883 A | 10/1992 | Griffith | |
| 5,234,956 A | 8/1993 | Lipton | |
| 5,334,618 A | 8/1994 | Lipton | |
| 5,455,279 A | 10/1995 | Lipton | |
| 5,506,231 A | 4/1996 | Lipton | |
| 5,614,560 A | 3/1997 | Lipton | |
| 5,747,545 A | 5/1998 | Lipton | |
| 5,801,203 A | 9/1998 | Lipton | |
| 5,804,374 A | 9/1998 | Baltimore et al. | |
| 6,071,876 A | 6/2000 | Lipton et al. | |
| 6,150,090 A | 11/2000 | Baltimore et al. | |
| 6,410,516 B1 | 6/2002 | Baltimore et al. | |
| 6,495,604 B1 | 12/2002 | Ichimori et al. | |
| 6,511,800 B1 | 1/2003 | Singh | |
| 7,078,540 B1 | 7/2006 | Tamura et al. | |
| 7,271,248 B2 | 9/2007 | Hardiman et al. | |
| 7,417,059 B2 | 8/2008 | Tamura et al. | |
| 7,670,603 B2 | 3/2010 | Hardiman et al. | |
| 7,863,263 B2 | 1/2011 | Ohmoto et al. | |
| 2002/0052019 A1 | 5/2002 | Goddard et al. | |
| 2002/0055173 A1 | 5/2002 | Parks et al. | |
| 2002/0086368 A1 | 7/2002 | Gurney | |
| 2003/0032090 A1 | 2/2003 | Hardiman et al. | |
| 2003/0087387 A1 | 5/2003 | Gurney | |
| 2003/0195256 A1 | 10/2003 | Singh | |
| 2003/0212114 A1 | 11/2003 | Sato | |
| 2004/0049041 A1 | 3/2004 | Ikemoto et al. | |
| 2004/0063685 A1 | 4/2004 | Itzawa et al. | |
| 2004/0072138 A1 | 4/2004 | Singh | |
| 2004/0171086 A1 | 9/2004 | Fink et al. | |
| 2004/0191833 A1 | 9/2004 | Fink et al. | |
| 2004/0214757 A1 | 10/2004 | Baltimore et al. | |
| 2004/0253276 A1 | 12/2004 | Sato et al. | |
| 2004/0259790 A1 | 12/2004 | Pulendran et al. | |
| 2005/0059072 A1 | 3/2005 | Birmachu et al. | |

(Continued)

FOREIGN PATENT DOCUMENTS

| | | |
|---|---|---|
| EP | 1 063 228 A1 | 12/2000 |
| EP | 1 209 149 A1 | 5/2002 |

(Continued)

OTHER PUBLICATIONS

Joseph (Oxaliplatin Acts on IB-4-Postive Nociceptors to induce an Oxidative Stress-Dependent Acute Painful Peripheral Neuropathy, The Journal of Pain, vol. 9, No. 5, 2008 pp. 463-472).*

Bettoni et al., "Glial TLR4 Receptor as New Target to Treat Neuropathic Pain: Efficacy of a New Receptor Antagonist in a Model of Peripheral Nerve Injury in Mice," GLIA, Sep. 2008, 56(12)1 312-1319.

Fairman et al., "Blockade of Stimulated Rat Microglial, Macrophage and Human Peripheral Blood Mononuclear Cell (PBMC) Toll-Like Receptor 4 (TLR4), Significantly and Completely Reverses Proinflammatory Cytokine Release, Potential Therapeutic Target for Inflammatory & Neuropathic Pain," 13th World Congress on Pain, Abstract of Presentation No. PW 140, presented Sep. 1, 2010, abstract published Jun. 4. 2010, 2 pages.

(Continued)

Primary Examiner — San-Ming Hui
Assistant Examiner — Kathrien Cruz
(74) Attorney, Agent, or Firm — Foley & Lardner LLP

(57) ABSTRACT

The present invention provides a medicament that suppresses (or mitigates) various neurological symptoms caused by a peripheral nerve disorder induced by an anti-cancer agent.

9 Claims, No Drawings

(56) References Cited

U.S. PATENT DOCUMENTS

| | | |
|---|---|---|
| 2005/0112659 A1 | 5/2005 | Hardiman et al. |
| 2005/0176783 A1 | 8/2005 | Tamura et al. |
| 2005/0272701 A1 | 12/2005 | Asakawa et al. |
| 2006/0063709 A1 | 3/2006 | Baltimore et al. |
| 2007/0027094 A1 | 2/2007 | Singh |
| 2007/0244066 A1 | 10/2007 | DeLeo et al. |
| 2008/0025974 A1 | 1/2008 | Hardiman et al. |
| 2008/0166763 A1 | 7/2008 | Gurney |
| 2008/0194800 A1 | 8/2008 | Hardiman et al. |
| 2008/0199477 A1 | 8/2008 | Hardiman et al. |
| 2008/0227846 A1 | 9/2008 | Singh et al. |
| 2008/0242634 A1 | 10/2008 | Perez-Polo |
| 2008/0275104 A1 | 11/2008 | Singh et al. |
| 2009/0062355 A1 | 3/2009 | Iizawa et al. |
| 2009/0105314 A1 | 4/2009 | Ii et al. |
| 2009/0192120 A1 | 7/2009 | Singh |
| 2009/0220427 A1 | 9/2009 | Mor |
| 2009/0227644 A1 | 9/2009 | Ohmoto et al. |
| 2009/0317833 A1 | 12/2009 | Hazeki et al. |
| 2010/0016381 A1 | 1/2010 | Asakawa et al. |
| 2010/0239523 A1 | 9/2010 | Watkins et al. |
| 2010/0266599 A1 | 10/2010 | Hardiman et al. |
| 2011/0059920 A1 | 3/2011 | Ohmoto et al. |
| 2011/0184034 A1 | 7/2011 | Ii et al. |
| 2011/0237662 A1 | 9/2011 | Singh |
| 2012/0178774 A1 | 7/2012 | Yin et al. |

FOREIGN PATENT DOCUMENTS

| | | |
|---|---|---|
| EP | 1 495 756 A1 | 1/2005 |
| EP | 1 524 263 | 4/2005 |
| EP | 2 018 872 A1 | 1/2009 |
| EP | 2 039 681 A1 | 3/2009 |
| EP | 2 260 869 A2 | 12/2010 |
| EP | 2 366 389 A1 | 9/2011 |
| WO | WO 87/04170 A1 | 7/1987 |
| WO | WO 88/05083 A1 | 7/1988 |
| WO | WO 89/07614 A1 | 8/1989 |
| WO | WO 89/08147 A1 | 9/1989 |
| WO | WO 90/11761 A1 | 10/1990 |
| WO | WO 91/04023 A1 | 4/1991 |
| WO | WO 92/03137 A1 | 3/1992 |
| WO | WO 92/17168 A1 | 10/1992 |
| WO | WO 92/18112 A1 | 10/1992 |
| WO | WO 94/05275 A1 | 3/1994 |
| WO | WO 99/20756 A2 | 4/1999 |
| WO | WO 99/26657 A1 | 6/1999 |
| WO | WO 99/46242 A1 | 9/1999 |
| WO | WO 01/10826 A1 | 2/2001 |
| WO | WO 01/56562 A1 | 8/2001 |
| WO | WO 01/90151 A2 | 11/2001 |
| WO | WO 02/13816 A1 | 2/2002 |
| WO | WO 02/32859 A1 | 4/2002 |
| WO | WO 02/45470 A1 | 6/2002 |
| WO | WO 03/013513 A1 | 2/2003 |
| WO | WO 03/084527 A1 | 10/2003 |
| WO | WO 03/092675 A1 | 11/2003 |
| WO | WO 2004/074435 A2 | 9/2004 |
| WO | WO 2004/075865 A2 | 9/2004 |
| WO | WO 2004/087049 A2 | 10/2004 |
| WO | WO 2004/098505 A2 | 11/2004 |
| WO | WO 2005/029037 A2 | 3/2005 |
| WO | WO 2005/062854 A2 | 7/2005 |
| WO | WO 2006/118329 A1 | 11/2006 |
| WO | WO 2006/129788 A1 | 12/2006 |
| WO | WO 2007/071621 A1 | 6/2007 |
| WO | WO 2007/091790 A1 | 8/2007 |
| WO | WO 2007/100650 A2 | 9/2007 |
| WO | WO 2007/114296 A1 | 10/2007 |
| WO | WO 2007/123186 A1 | 11/2007 |
| WO | WO 2007/132825 A1 | 11/2007 |
| WO | WO 2008/004673 A1 | 1/2008 |
| WO | WO 2009/059050 A2 | 5/2009 |
| WO | WO 2009/145814 A2 | 12/2009 |
| WO | WO 2011/038152 A2 | 3/2011 |

OTHER PUBLICATIONS

Il et al., "A Novel Cyclohexene Derivative, Ethyl (6R)-6-[N-(2-Chloro-4-fluorophenyl)sulfamoyl]cyclohex-1-ene-1-carboxylate (TAK-242), Selectively Inhibits Toll-Like Receptor 4-Mediated Cytokine Production through Suppression of Intracellular Signaling," Molecular Pharmacology, 2006, 69(4):1288-1295.

Lewis et al., "Evidence that Intrathecal Morphine-3-Glucuronide May Cause Pain Enhancement Via Toll-like Receptor 4/MD-2 and Interleukin-1β," Neuroscience, Jan. 20, 2010, 165(2):569-583.

Miyajima et al., "Spin Trapping Agent, Phenyl N-*Tert*-Butyl Nitrone, Inhibits Induction of Nitric Oxide Synthase in Endotoxin-induced Shock in Mice," Biochem. Biophy. Research Commun., Oct. 4, 1995, 215(1):114-121.

Schini-Kerth et al., "N-α-Tosyl-L-Lysine Chloromethylketone Prevents Expression of iNOS in Vascular Smooth Muscle by Blocking Activation of NF-κB," Arteriosclerosis, Thrombosis, and Vascular Biology, Apr. 1997, 17(4): 672-679.

Tanga et al., "The CNS role of Toll-like receptor 4 in innate neuroimmunity and painful neuropathy," PNAS, Apr. 19, 2005, 102(16):5856-5861.

Wang et al., "Morphine activates neuroinflammation in a manner parallel to endotoxin," PNAS, Apr. 17, 2012, 109(16):6325-6330.

Lynch et al., "Attenuation of mechanical allodynia by clinically utilized drugs in a rat chemotherapy-induced neuropathic pain model," Pain, Jul. 1, 2004, 110(1-2):56-63.

Rao et al., "Efficacy of Gabapentin in the Management of Chemotherapy-induced Peripheral Neuropathy," Cancer, Nov. 1, 2007, 110(9):2110-2118.

Wolf et al., "Chemotherapy-induced peripheral neuropathy: Prevention and treatment strategies," European Journal of Cancer, Jul. 1, 2008, 44(11):1507-1515.

Ling et al., "Comparative antiallodynic activity of morphine, pregabalin and lidocaine in a rat model of neuropathic pain produced by one oxaliplatin injection," Neuropharmacology, 2008, 55:724-728.

Polomano et al., "A painful peripheral neuropathy in the rat produced by the chemotherapeutic drug, paclitaxel," Pain, 2001, 94:293-304.

* cited by examiner ations. Even when the treatment is stopped,
sequelae of continued neurological symptoms such as numbness and the like often remain.

In view of the above, neurological symptoms (e.g., dysesthesia such as numbness, pain and the like) by peripheral nerve disorders caused by the administration of an anti-cancer agent form a dose limiting factor of various anti-cancer agents, and the development of a therapeutic drug for mitigating these neurological symptoms associated with a treatment with an anti-cancer agent has been desired (non-patent document 1 and non-patent document 2).

While pain plays the most important role for biological defense, it is also well known to bring an invasive severe pain represented by a neuropathic pain, which exceeds the level of its role and unnecessary for the body. The neuropathic pain is a severe pain that continues even after a complete cure of an injured tissue including peripheral and central nervous systems, which includes hyperalgesia in which even a mild pain stimulation is felt as a severe pain, spontaneous pain accompanying uncomfortable dysesthesia, allodynia in which even a light contact stimulation that does not develop a pain in itself causes a pain and the like.

It has long been unclear in which site such neuropathic pain is expressed by what mechanism. However, some neuropathic pain animal models have been developed in recent years, and the elucidation of the onset mechanism thereof is ongoing. The representative models include the spinal cord nerve ligation model by Kim and Chung (non-patent document 3), the sciatic nerve partial ligation model by Seltzer et al. (non-patent document 4), the model with gentle ligation of the sciatic nerve at several sites by Bennett et al. (non-patent document 5), the model with ligation and cleavage of tibial nerve and whole sural nerve, leaving the sural nerve, by Decosterd and Woolf (non-patent document 6) and the like, all of which creates pathology similar to human chronic neuropathic pain by causing peripheral nerve disorders.

It has been clarified by the analysis of these animal models that the development of neuropathic pain includes one caused by changes in the peripheral nerve such as a sustained increase in the sensitivity or spontaneous firing and the like of the peripheral nerve starting from a peripheral nerve disorder (non-patent document 7), and one caused by changes in the spinal cord or highest center (non-patent document 8). The changes in the spinal cord are caused by activation of microglia, and factors such as cytokine and the like produced and liberated from the activated microglia are considered to stimulate secondary neuron and enhance pain sensitivity.

It has been reported, moreover, that incidents similar to those in neuropathic pain model also occur in animal models of neurological symptoms caused by the administration of an anti-cancer agent. That is, by the administration of an anti-cancer agent such as paclitaxel, vinblastine and the like, hyperalgesia occurs along with a peripheral nerve disorder (non-patent document 9), and microglia is activated in the spinal cord (non-patent document 10). From the above, it is considered that the expression mechanism similar to that in neuropathic pain is also involved in the expression of neurological symptoms in human, which is due to peripheral nerve disorders caused by the administration of an anti-cancer agent.

Patent document 1 describes that (i) a compound represented by the formula:

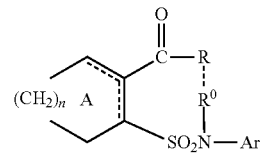

wherein
R is an aliphatic hydrocarbon group optionally having substituent(s), an aromatic hydrocarbon group optionally having substituent(s), a heterocyclic group optionally having substituent(s), a group represented by the formula: —OR$^1$ wherein R$^1$ is a hydrogen atom or an aliphatic hydrocarbon group optionally having substituent(s), or a group represented by the formula:

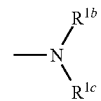

wherein $R^{1b}$ is a hydrogen atom or an aliphatic hydrocarbon group optionally having substituent(s), and $R^{1c}$ is the same as or different from $R^{1b}$, a hydrogen atom or an aliphatic hydrocarbon group optionally having substituent(s), $R^0$ is a hydrogen atom or an aliphatic hydrocarbon group, or R and $R^0$ in combination form a bond, ring A is a cycloalkene substituted by 1 to 4 substituents selected from (1) an aliphatic hydrocarbon group optionally having substituent(s), (2) an aromatic hydrocarbon group optionally having substituent(s), (3) a group represented by the formula: —$OR^{11}$ wherein $R^{11}$ is a hydrogen atom or an aliphatic hydrocarbon group optionally having substituent(s), and (4) a halogen atom, Ar is an aromatic hydrocarbon group optionally having substituent(s), a group represented by the formula:

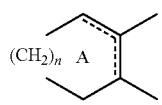

is a group represented by the formula:

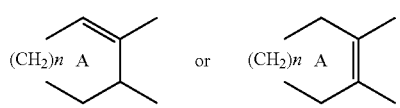

and n is an integer of 1 to 4, and (ii) a compound represented by the formula:

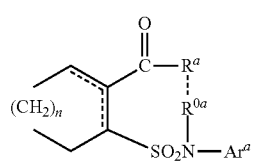

(Ie)

wherein $R^a$ is an aliphatic hydrocarbon group optionally having substituent(s), an aromatic hydrocarbon group optionally having substituent(s), a heterocyclic group optionally having substituent(s), a group represented by the formula: —$OR^{1a}$ wherein $R^{1a}$ is a hydrogen atom or an aliphatic hydrocarbon group optionally having substituent(s), or a group represented by the formula:

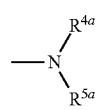

wherein $R^{4a}$ and $R^{5a}$ are the same or different and each is a hydrogen atom or an aliphatic hydrocarbon group optionally having substituent(s), $R^{0a}$ is a hydrogen atom or an aliphatic hydrocarbon group, or $R^a$ and $R^{0a}$ in combination form a bond, $Ar^a$ is an aromatic hydrocarbon group optionally having substituent(s), a group represented by the formula:

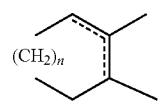

is a group represented by the formula:

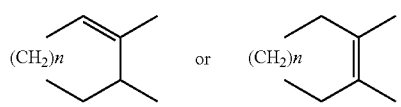

and n is an integer of 1 to 4, a salt thereof and a prodrug thereof have a nitric oxide (NO) production-inhibiting effect and an inhibitory effect on the production of inflammatory cytokines, such as TNF-α, IL-1, IL-6 and the like, and are useful as an agent for the prophylaxis or treatment of diseases including cardiac diseases, autoimmune diseases, inflammatory diseases, central nervous system diseases, infectious diseases, sepsis, septic shock and the like; and Patent document 2 describes that a compound represented by the formula:

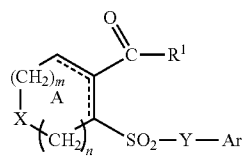

wherein $R^1$ is an aliphatic hydrocarbon group optionally having substituent(s), an aromatic hydrocarbon group optionally having substituent(s), a heterocyclic group optionally having substituent(s), a group represented by the formula: —$OR^{1a}$ wherein $R^{1a}$ is a hydrogen atom or an aliphatic hydrocarbon group optionally having substituent(s), or a group represented by the formula:

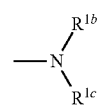

wherein $R^{1b}$ and $R^{1c}$ are the same or different and each is a hydrogen atom or an aliphatic hydrocarbon group optionally having substituent(s), X is methylene, NH, a sulfur atom or an oxygen atom, Y is methylene optionally having substituent(s) or NH optionally having substituent(s), ring A is a 5- to 8-membered ring optionally having 1 to 4 substituents selected from the group consisting of (1) an aliphatic hydrocarbon group optionally having substituent(s), (2) an aromatic hydrocarbon group optionally having substituent(s), (3) a group represented by the formula: —$OR^2$ wherein $R^2$ is a hydrogen atom or an aliphatic hydrocarbon group optionally having substituent(s), and (4) a halogen atom, Ar is an aromatic hydrocarbon group optionally having substituent(s), a group represented by the formula:

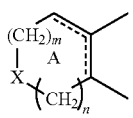

is a group represented by the formula:

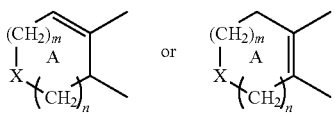

m is an integer of 0 to 2,
n is an integer of 1 to 3, and
the total of m and n is 4 or less;
provided that when X is a methylene group, then Y should be a methylene group optionally having substituent(s), a salt thereof and a prodrug thereof
have a nitric oxide (NO) production-inhibiting effect and an inhibitory effect on the production of inflammatory cytokines, such as TNF-α, IL-1, IL-6 and the like, and are useful as an agent for the prophylaxis or treatment of diseases including cardiac diseases, autoimmune diseases, inflammatory diseases, central nervous system diseases, infectious diseases, sepsis, septic shock and the like.

Patent document 11 describes that the compounds described in the above-mentioned patent document 1 and/or patent document 2 have a TLR (particularly, TLR4) signal inhibitory action, and are useful as an agent for suppressing production or expression of a factor selected from IL-2 (Interleukin-2), IL-3, IL-8, IL-10, IL-12, IL-17, MIP-2 (macrophage inflammatory protein-2), KC (keratinocyte derived-chemokine), GM-CSF (granulocyte-macrophage colony-stimulating factor), IFN (interferon)-γ and prostaglandin E2 and the like, and the like.

Patent documents 3-13 describe that the compounds described in the above-mentioned patent document 1 and/or patent document 2 can be used for the treatment of pain.

However, patent documents 1-13 do not describe that the compounds described in the above-mentioned patent document 1 and/or patent document 2 can suppress peripheral nerve disorders induced by anti-cancer agents.

DOCUMENT LIST

Patent Documents patent document 1: WO99/46242
patent document 2: WO01/10826
patent document 3: WO01/56562
patent document 4: WO02/13816
patent document 5: WO02/32859
patent document 6: WO03/013513
patent document 7: WO02/45750
patent document 8: WO03/084527
patent document 9: WO2006/118329
patent document 10: WO2007/114296
patent document 11: WO2007/123186
patent document 12: WO2007/132825
patent document 13: WO2008/004673

Non-Patent Documents non-patent document 1: Beinert T, Masuhr F, Mwela E, Schweigert M, Flath B, Harder H, et al. Neuropathy under chemotherapy. Eur J Med Res 2000; 5: 415-23.

non-patent document 2: Cavaliere R, Schiff D. Neurologic toxicities of cancer therapies. Curr Neurol Neurosci Rep 2006; 6: 218-26.

non-patent document 3: Kim S H, Chung J M. An experimental model for peripheral neuropathy produced by segmental spinal nerve ligation in the rat. Pain 1992; 50: 355-363.

non-patent document 4: Seltzer Z, Dubner R, Shir Y. A novel behavioral model of neuropathic pain disorders produced in rats by partial sciatic nerve injury. Pain 1990; 43: 205-218.

non-patent document 5: Bennett G J, Xei Y-K. A peripheral mononeuropathy in rat that produces disorders of pain sensation like those seen in man. Pain 1988; 33: 87-107.

non-patent document 6: Decosterd I, Woolf C J. Spared nerve injury: an animal model of persistent peripheral neuropathic pain. Pain 2000; 87: 149-158.

non-patent document 7: Campbell, J. N. & Meyer, R. A. Mechanisms of neuropathic pain. Neuron 2006; 52, 77-92.

non-patent document 8: Scholz, J. & Woolf, C. J. The neuropathic pain triad: neurons, immunocytes, and glia. Nature Neurosci. 2007; 10: 1361-1368.

non-patent document 9: Siau C, Xiao W H, Bennett G J. Paclitaxel- and vincristine-evoked painful peripheral neuropathies: loss of epidermal innervation and activation of Langerhans cells. Exptl Neurol 2006; 201: 507-514.

non-patent document 10: Norikazu Kiguchi, Takehiko Maeda, Yuka Kobayashi, Shiroh Kishioka. Up-regulation of tumor necrosis factor-alpha in spinal cord contributes to vincristine-induced mechanical allodynia in mice. Neuroscience Letters 2008; 445: 140-143.

SUMMARY OF THE INVENTION

Problems to be Solved by the Invention

The present invention aims to provide a medicament for suppressing (or mitigating) neurological symptoms (e.g., dysesthesia such as numbness, pain and the like) due to peripheral nerve disorders which are one of the side effects caused by the administration of anti-cancer agents.

Means of Solving the Problems

The present inventors have conducted intensive studies in an attempt to solve the aforementioned problems and found that the compounds represented by the below-mentioned formula (I), formula (II) and formula (III) unexpectedly suppress (or mitigate) neurological symptoms of peripheral nerve disorders caused by anti-cancer agents. Further studies made by the present inventors based on these findings have resulted in the completion of the present invention.

Accordingly, the present invention relates to

[1] An agent for suppressing a peripheral nerve disorder induced by an anti-cancer agent, which comprises a compound represented by the formula (I):

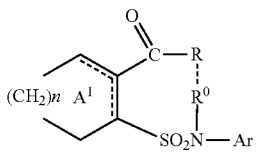

(I)

wherein
R is
(1) an aliphatic hydrocarbon group optionally having substituent(s),
(2) an aromatic hydrocarbon group optionally having substituent(s),
(3) a heterocyclic group optionally having substituent(s),
(4) a group represented by the formula: —$OR^1$ wherein $R^1$ is a hydrogen atom or an aliphatic hydrocarbon group optionally having substituent(s), or
(5) a group represented by the formula:

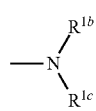

wherein $R^{1b}$ and $R^{1c}$ are the same or different and each is a hydrogen atom or an aliphatic hydrocarbon group optionally having substituent(s),
$R^0$ is a hydrogen atom or an aliphatic hydrocarbon group, or R and
$R^0$ in combination may form a bond,
ring $A^1$ is a cycloalkene optionally substituted by 1 to 4 substituents selected from the group consisting of
(i) an aliphatic hydrocarbon group optionally having substituent(s),
(ii) an aromatic hydrocarbon group optionally having substituent(s),
(iii) a group represented by the formula: —$OR^{11}$ wherein $R^{11}$ is a hydrogen atom or an aliphatic hydrocarbon group optionally having substituent(s), and
(iv) a halogen atom,
Ar is an aromatic hydrocarbon group optionally having substituent(s),
a group represented by the formula:

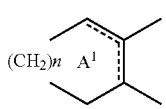

is a group represented by the formula:

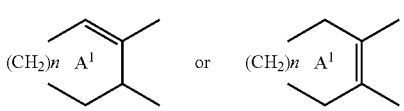

and n is an integer of 1 to 4,
or a salt thereof or a prodrug thereof, or a compound represented by the formula (II):

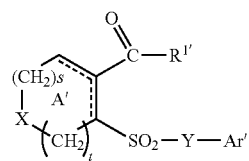

(II)

wherein
$R^{1'}$ is
(1) an aliphatic hydrocarbon group optionally having substituent(s),
(2) an aromatic hydrocarbon group optionally having substituent(s),
(3) a heterocyclic group optionally having substituent(s),
(4) a group represented by the formula: —$OR^{1a'}$ wherein $R^{1a'}$ is a hydrogen atom or an aliphatic hydrocarbon group optionally having substituent(s), or
(5) a group represented by the formula:

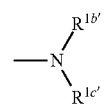

(a)

wherein $R^{1b'}$ and $R^{1c'}$ are the same or different and each is a hydrogen atom or an aliphatic hydrocarbon group optionally having substituent(s),
X is methylene, NH, a sulfur atom or an oxygen atom,
Y is methylene optionally having substituent(s) or NH optionally having substituent(s),
ring A' is a 5- to 8-membered ring optionally having 1 to 4 substituents selected from the group consisting of
(i) an aliphatic hydrocarbon group optionally having substituent(s),
(ii) an aromatic hydrocarbon group optionally having substituent(s),
(iii) a group represented by the formula: —$OR^{2'}$ wherein $R^{2'}$ is a hydrogen atom or an aliphatic hydrocarbon group optionally having substituent(s), and
(iv) a halogen atom,
Ar' is an aromatic hydrocarbon group optionally having substituent(s),
a group represented by the formula:

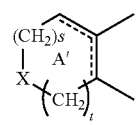

(b)

is a group represented by the formula:

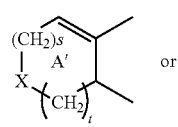

(b1)

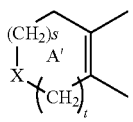

s is an integer of 0 to 2,
t is an integer of 1 to 3, and
the total of s and t is 4 or less;
provided that when X is methylene, then Y should be methylene optionally having substituent(s),
or a salt thereof or a prodrug thereof;

[2] an agent for suppressing a peripheral nerve disorder induced by an anti-cancer agent, comprising a compound represented by the formula (III):

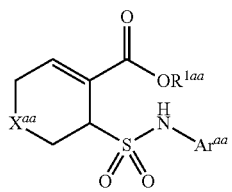

wherein $R^{1aa}$ is $C_{1-6}$ alkyl,
$X^{aa}$ is methylene or an oxygen atom, and
$Ar^{aa}$ is phenyl optionally having 1 or 2 substituents selected from a halogen atom, $C_{1-6}$ alkyl and $C_{1-6}$ alkoxy,
or a salt thereof or a prodrug thereof;

[3] the agent of the above-mentioned [1] or [2], comprising ethyl (6R)-6-[N-(2-chloro-4-fluorophenyl)sulfamoyl]-1-cyclohexene-1-carboxylate or a salt thereof or a prodrug thereof;

[4] the agent of the above-mentioned [1] or [2], comprising ethyl (3S)-3-[N-(2-chloro-4-fluorophenyl)sulfamoyl]-3,6-dihydro-2H-pyran-4-carboxylate or a salt thereof or a prodrug thereof;

[5] the agent of the above-mentioned [1] or [2], wherein the anti-cancer agent is selected from paclitaxel, docetaxel, vincristine, cisplatin, carboplatin and bortezomib;

[5a] the agent of the above-mentioned [1] or [2], wherein the anti-cancer agent is selected from paclitaxel, vincristine, cisplatin, carboplatin and bortezomib;

[6] the agent of the above-mentioned [5], wherein the anti-cancer agent is paclitaxel.

Effect of the Invention

According to the present invention, neurological symptoms (e.g., dysesthesia such as numbness, pain and the like) due to peripheral nerve disorders which are one of the side effects caused by the administration of an anti-cancer agent can be suppressed (or mitigated).

In addition, according to the present invention, a decrease in the dosage due to the side effects of the administration of an anti-cancer agent can be avoided.

According to the present invention, moreover, a treatment at a high dose, which has been impossible heretofore, can be enabled by controlling the side effects of the administration of an anti-cancer agent.

According to the present invention, moreover, a long-term treatment with an anti-cancer agent, while maintaining the QOL of patients, can be enabled by controlling the side effects of the administration of an anti-cancer agent.

DETAILED DESCRIPTION OF THE INVENTION

The compound represented by the formula (I) is explained.

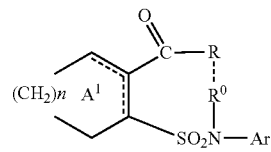

R is
(1) an aliphatic hydrocarbon group optionally having substituent(s),
(2) an aromatic hydrocarbon group optionally having substituent(s),
(3) a heterocyclic group optionally having substituent(s),
(4) a group represented by the formula: —$OR^1$ wherein $R^1$ is a hydrogen atom or an aliphatic hydrocarbon group optionally having substituent(s), or
(5) a group represented by the formula:

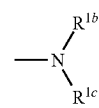

wherein $R^{1b}$ and $R^{1c}$ are the same or different and each is a hydrogen atom or an aliphatic hydrocarbon group optionally having substituent(s), or R and $R^0$ in combination form a bond, with particular preference given to the group represented by the formula: —$OR^1$ wherein $R^1$ is as defined above.

$R^0$ is a hydrogen atom or an aliphatic hydrocarbon group.

When R and $R^0$ in combination form a bond, the compound represented by the formula (I) can be represented by the formula:

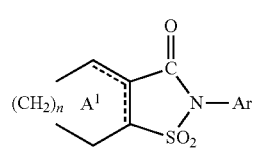

wherein each symbol is as defined above, and specifically can be represented by the formula:

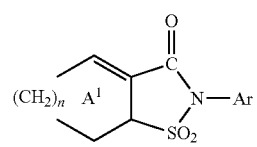

wherein each symbol is as defined above, or

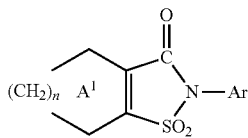
(Iii)

wherein each symbol is as defined above.

When R is a group represented by the formula: —OR$^1$ wherein R$^1$ is as defined above, the compound represented by the formula (I) can be represented by the formula:

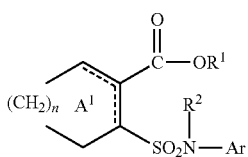
(Ibb′)

wherein R$^2$ is a hydrogen atom or an aliphatic hydrocarbon group, and other symbols are as defined above, and specifically can be represented by the formula:

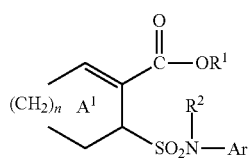
(Inn)

wherein each symbol is as defined above, or

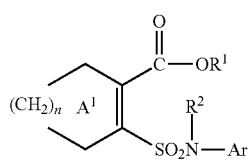
(Ioo)

wherein each symbol is as defined above.

As the compound represented by the formula (I), a compound represented by the formula (Icc) or the formula (Inn) is preferable.

As the "aliphatic hydrocarbon group" of the "aliphatic hydrocarbon group optionally having substituent(s)" for R, R$^1$, R$^{1l}$, R$^{1b}$ or R$^{1c}$ and the "aliphatic hydrocarbon group" for R$^0$ or R$^2$, for example, alkyl, cycloalkyl, cycloalkylalkyl, alkenyl, alkynyl, etc. are preferable.

As alkyl, for example, linear or branched alkyl having 1 to 20 carbon atoms (e.g., methyl, ethyl, n-propyl, isopropyl, n-butyl, isobutyl, sec-butyl, tert-butyl, pentyl, hexyl, heptyl, octyl, nonyl, decyl, dodecyl) and the like are preferable, and particularly, for example, lower alkyl having 1 to 6 carbon atoms (e.g., methyl, ethyl, n-propyl, isopropyl, n-butyl, isobutyl, sec-butyl, tert-butyl) and the like are preferable.

As cycloalkyl, for example, cycloalkyl having a carbon number of 3 to 10 (e.g., cyclopropyl, cyclobutyl, cyclopentyl, cyclohexyl, cycloheptyl, cyclooctyl) and the like are preferable and, in particular, for example, cycloalkyl having a carbon number of 3 to 6 (e.g., cyclopropyl, cyclobutyl, cyclopentyl, cyclohexyl) and the like are preferable.

As cycloalkylalkyl, for example, cycloalkylalkyl having a carbon number of 4 to 12 (e.g., cyclopropylmethyl, cyclopentylmethyl, cyclohexylmethyl, cycloheptylmethyl) and the like are preferable and, in particular, for example, cycloalkylalkyl having a carbon number 4 to 8 (particularly 4 to 7) (e.g., cyclopropylmethyl, cyclopentylmethyl, cyclohexylmethyl) and the like are preferable.

As alkenyl, for example, lower alkenyl having a carbon number of 3 to 6 (e.g., propenyl, butenyl, pentenyl) and the like are preferable and, in particular, for example, lower alkenyl having a carbon number of 3 or 4 (e.g., propenyl, butenyl) and the like are preferable.

As alkynyl, for example, lower alkynyl having a carbon number of 3 to 6 (e.g., propynyl, butynyl, pentynyl) and the like are preferable and, in particular, for example, lower alkynyl having a carbon number of 3 or 4 (e.g., propynyl, butynyl) and the like are preferable.

As the "substituent" of the aforementioned "aliphatic hydrocarbon group optionally having substituent(s)", for example,
(1) a heterocyclic group,
(2) an oxo group,
(3) hydroxy,
(4) $C_{1-6}$ alkoxy,
(5) $C_{3-10}$ (particularly $C_{3-6}$) cycloalkyloxy,
(6) $C_{6-10}$ aryloxy,
(7) $C_{7-19}$ (particularly $C_{7-12}$) aralkyloxy,
(8) heterocyclyloxy,
(9) $C_{1-6}$ alkylthio (the sulfur atom is optionally oxidized),
(10) $C_{3-10}$ (particularly $C_{3-6}$) cycloalkylthio (the sulfur atom is optionally oxidized),
(11) $C_{6-10}$ arylthio (the sulfur atom is optionally oxidized),
(12) $C_{7-19}$ (particularly $C_{7-12}$) aralkylthio (the sulfur atom is optionally oxidized),
(13) heterocyclylthio,
(14) heterocyclylsulfinyl,
(15) heterocyclylsulfonyl,
(16) nitro,
(17) a halogen atom,
(18) cyano,
(19) carboxy,
(20) $C_{1-10}$ (particularly $C_{1-6}$) alkoxy-carbonyl,
(21) $C_{3-6}$ cycloalkyloxy-carbonyl,
(22) $C_{6-10}$ aryloxy-carbonyl,
(23) $C_{7-19}$ (particularly $C_{7-12}$) aralkyloxy-carbonyl,
(24) heterocyclyloxycarbonyl,
(25) $C_{6-10}$ aryl-carbonyl,
(26) $C_{1-6}$ alkanoyl,
(27) $C_{3-5}$ alkenoyl,
(28) $C_{6-10}$ aryl-carbonyloxy,
(29) $C_{2-6}$ alkanoyloxy,
(30) $C_{3-5}$ alkenoyloxy,
(31) carbamoyl optionally having substituent(s),
(32) thiocarbamoyl optionally having substituent(s),
(33) carbamoyloxy optionally having substituent(s),
(34) $C_{1-6}$ alkanoylamino,
(35) $C_{6-10}$ aryl-carbonylamino,
(36) $C_{1-10}$ (particularly $C_{1-6}$) alkoxy-carboxamido,
(37) $C_{6-10}$ aryloxy-carboxamido,
(38) $C_{7-19}$ (particularly $C_{7-12}$) aralkyloxy-carboxamido,
(39) $C_{1-10}$ (particularly $C_{1-6}$) alkoxy-carbonyloxy,
(40) $C_{6-10}$ aryloxy-carbonyloxy,
(41) $C_{7-19}$ (particularly $C_{7-12}$) aralkyloxy-carbonyloxy,

(42) $C_{3-10}$ (particularly $C_{3-6}$) cycloalkyloxy-carbonyloxy,
(43) ureido optionally having substituent(s),
(44) $C_{3-10}$ aryl optionally having substituent(s) and the like are used.

These substituents are substituted at substitutable positions of the aforementioned "aliphatic hydrocarbon group". They are not limited to a single substituent, but may be the same or different, and more than one substituent (preferably 2 to 4) may be used.

As "$C_{1-6}$ alkoxy", for example, methoxy, ethoxy, n-propoxy, isopropoxy, n-butoxy, tert-butoxy, n-pentyloxy, n-hexyloxy and the like are used.

As "$C_{3-10}$ cycloalkyloxy", for example, cyclopropyloxy, cyclohexyloxy and the like are used.

As "$C_{6-10}$ aryloxy", for example, phenoxy, naphthyloxy and the like are used.

As "$C_{7-19}$ aralkyloxy", for example, benzyloxy, 1-phenylethyloxy, 2-phenylethyloxy, benzhydryloxy, 1-naphthylmethyloxy and the like are used.

As "$C_{1-6}$ alkylthio (the sulfur atom is optionally oxidized)", for example, methylthio, ethylthio, n-propylthio, n-butylthio, methylsulfinyl, methylsulfonyl and the like are used.

As "$C_{3-10}$ cycloalkylthio (the sulfur atom is optionally oxidized)", for example, cyclopropylthio, cyclohexylthio, cyclopentylsulfinyl, cyclohexylsulfonyl and the like are used.

As "$C_{6-10}$ arylthio (the sulfur atom is optionally oxidized)", for example, phenylthio, naphthylthio, phenylsulfinyl, phenylsulfonyl and the like are used.

As "$C_{7-19}$ aralkylthio (the sulfur atom is optionally oxidized)", for example, benzylthio, phenylethylthio, benzhydrylthio, benzylsulfinyl, benzylsulfonyl and the like are used.

As the "halogen atom", for example, a fluorine atom, a chlorine atom, a bromine atom and an iodine atom are used.

As "$C_{1-10}$ alkoxy-carbonyl", for example, methoxycarbonyl, ethoxycarbonyl, n-propoxycarbonyl, isopropoxycarbonyl, n-butoxycarbonyl, isobutoxycarbonyl, tert-butoxycarbonyl and the like are used.

As "$C_{3-6}$ cycloalkyloxy-carbonyl", for example, cyclopropyloxycarbonyl, cyclopentyloxycarbonyl, cyclohexyloxycarbonyl and the like are used.

As "$C_{6-10}$ aryloxy-carbonyl", for example, phenoxycarbonyl, naphthyloxycarbonyl and the like are used.

As "$C_{7-19}$ aralkyloxy-carbonyl", for example, benzyloxycarbonyl, benzhydryloxycarbonyl, 2-phenethyloxycarbonyl and the like are used.

As "$C_{6-10}$ aryl-carbonyl", for example, benzoyl group, naphthoyl group and the like are used.

As "$C_{1-6}$ alkanoyl", for example, formyl, acetyl, propionyl, butyryl group, valeryl group, pivaloyl group and the like are used.

As "$C_{3-5}$ alkenoyl", for example, acryloyl, crotonoyl and the like are used, as the "$C_{6-10}$ aryl-carbonyloxy", for example, benzoyloxy, naphthoyloxy and the like are used.

As "$C_{2-6}$ alkanoyloxy", for example, acetoxy, propionyloxy, butyryloxy, valeryloxy, pivaloyloxy and the like are used.

As "$C_{3-5}$ alkenoyloxy", for example, acryloyloxy, crotonoyloxy and the like are used.

As "carbamoyl optionally having substituent(s)", for example, carbamoyl or cyclic amino (e.g., pyrrolidinyl, piperidinyl, piperazinyl, morpholinyl)carbonyl or the like, which is optionally substituted by one or the same or different two substituents selected from
(i) $C_{1-4}$ alkyl (e.g., methyl, ethyl),
(ii) phenyl,
(iii) $C_{1-7}$ acyl (e.g., acetyl, propionyl, benzoyl),
(iv) $C_{1-4}$ alkoxy-phenyl (e.g., methoxyphenyl), and the like is used, and specifically, for example, carbamoyl, N-methylcarbamoyl, N-ethylcarbamoyl, N,N-dimethylcarbamoyl, N,N-diethylcarbamoyl, N-phenylcarbamoyl, N-acetylcarbamoyl, N-benzoylcarbamoyl, N-(p-methoxyphenyl)carbamoyl, 1-pyrrolidinylcarbonyl, piperidinocarbonyl, 1-piperazinylcarbonyl, morpholinocarbonyl and the like are used.

As "thiocarbamoyl optionally having substituent(s)", thiocarbamoyl optionally substituted by one or the same or different two substituents selected from
(i) $C_{1-4}$ alkyl (e.g., methyl, ethyl),
(ii) phenyl, and the like is used, and specifically, for example, thiocarbamoyl, N-methylthiocarbamoyl, N-phenylthiocarbamoyl and the like are used.

As "carbamoyloxy optionally having substituent(s)", for example, carbamoyloxy optionally substituted by one or the same or different two substituents selected from
(i) $C_{1-4}$ alkyl (e.g., methyl, ethyl),
(ii) phenyl, and the like are used, and specifically, for example, carbamoyloxy, N-methylcarbamoyloxy, N,N-dimethylcarbamoyloxy, N-ethylcarbamoyloxy, N-phenylcarbamoyloxy and the like are used.

As "$C_{1-6}$ alkanoylamino", for example, an acetamido group, a propionamido group, a butyramido group, a valeramido group, a pivalamido group and the like are used.

As "$C_{6-10}$ aryl-carbonylamino", for example, a benzamido group, a naphthamido group, a phthalimido group and the like are used.

As "$C_{1-10}$ alkoxy-carboxamido", for example, methoxycarboxamido ($CH_3OCONH$—), ethoxycarboxamido, tert-butoxycarboxamido and the like are used.

As "$C_{6-10}$ aryloxy-carboxamido", for example, phenoxycarboxamido ($C_6H_5OCONH$—) and the like are used.

As "$C_{7-19}$ aralkyloxy-carboxamido", for example, benzyloxycarboxamido ($C_6H_5CH_2OCONH$—), benzhydryloxycarboxamido and the like are used.

As "$C_{1-10}$ alkoxy-carbonyloxy", for example, methoxycarbonyloxy, ethoxycarbonyloxy, n-propoxycarbonyloxy, isopropoxycarbonyloxy, n-butoxycarbonyloxy, tert-butoxycarbonyloxy, n-pentyloxycarbonyloxy, n-hexyloxycarbonyloxy and the like are used.

As "$C_{6-10}$ aryloxy-carbonyloxy", for example, phenoxycarbonyloxy, naphthyloxycarbonyloxy and the like are used.

As "$C_{7-19}$ aralkyloxy-carbonyloxy", for example, benzyloxycarbonyloxy, 1-phenylethyloxycarbonyloxy, 2-phenylethyloxycarbonyloxy, benzhydryloxycarbonyloxy and the like are used.

As "$C_{3-10}$ cycloalkyloxy-carbonyloxy", for example, cyclopropyloxycarbonyloxy, cyclohexyloxycarbonyloxy and the like are used.

As "ureido optionally having substituent(s)", for example, ureido optionally substituted by 1 to 3 (particularly 1 or 2) substituents selected from
(i) $C_{1-4}$ alkyl (e.g., methyl, ethyl),
(ii) phenyl, and the like is used and, for example, ureido, 1-methylureido, 3-methylureido, 3,3-dimethylureido, 1,3-dimethylureido, 3-phenylureido and the like are used. When two or more substituents are present, they may be the same or different.

When a heterocyclic group, heterocyclyloxy, heterocyclylthio, heterocyclylsulfinyl, heterocyclylsulfonyl or heterocyclyloxycarbonyl is used as the "substituent" of the "aliphatic hydrocarbon group optionally having substituent(s)", the heterocyclic group is a group obtained by removing one hydrogen atom bonded to the heterocycle, which is, for example, a 5- to 8-membered ring (particularly 5- or 6-membered ring) group containing 1 to several, preferably 1 to 4, hetero atoms such as a nitrogen atom (optionally oxidized), an oxygen atom, a sulfur atom and the like, or a fused ring group thereof. As such heterocyclic group, pyrrolyl, pyrazolyl, imidazolyl, 1,2,3-triazolyl, 1,2,4-triazolyl, tetrazolyl, furyl, thienyl, oxazolyl, isoxazolyl, 1,2,3-oxadiazolyl, 1,2,4-oxadiazolyl, 1,2,5-oxadiazolyl, 1,3,4-oxadiazolyl, thiazolyl, isothiazolyl, 1,2,3-thiadiazolyl, 1,2,4-thiadiazolyl, 1,2,5-thiadiazolyl, 1,3,4-thiadiazolyl, pyridyl, pyridazinyl, pyrimidinyl, pyrazinyl, indolyl, pyranyl, thiopyranyl, dioxinyl, dioxolyl, quinolyl, pyrido[2,3-d]pyrimidyl, 1,5-, 1,6-, 1,7-, 1,8-, 2,6- or 2,7-naphthyridyl, thieno[2,3-d]pyridyl, benzopyranyl, tetrahydrofuryl, tetrahydropyranyl, dioxolanyl, dioxanyl and the like are used.

These heterocyclic groups may be substituted at substitutable positions by 1 to 3 substituents selected from
(i) a $C_{1-4}$ alkyl (e.g., methyl, ethyl),
(ii) a hydroxy,
(iii) an oxo,
(iv) a $C_{1-4}$ alkoxy (e.g., methoxy, ethoxy, etc.), and the like. When two or more substituents are present, they may be the same or different.

As "$C_{6-10}$ aryl" of the "$C_{6-10}$ aryl optionally having substituent(s)", for example, phenyl, naphthyl, etc. can be used. The $C_{6-10}$ aryl may be substituted at a substitutable position by a substituent selected from those exemplified as the "substituent" (except for $C_{6-10}$ aryl optionally having substituent(s)) of the "aliphatic hydrocarbon group optionally having substituent(s)" described above. Such substituent is not limited to a single substituent, but the same or different, more than one (preferably 2 to 4) substituents may be used.

In the "aliphatic hydrocarbon group optionally having substituent(s)", the substituent may form, together with the aliphatic hydrocarbon group, an optionally substituted fused ring group, and as such fused ring group, indanyl, 1,2,3,4-tetrahydronaphthyl, etc. can be used. This fused ring group may be substituted at a substitutable position by a substituent selected from those exemplified as the "substituent" of the "aliphatic hydrocarbon group optionally having substituent(s)" described above. Such substituent substitutes at a substitutable position of the fused ring group, wherein the substituent is not limited to a single substituent, but the same or different, more than one (preferably 2 to 4) substituents may be used.

Among the above-mentioned "aliphatic hydrocarbon groups optionally having substituent(s)", preferable examples of R, $R^1$, $R^{11}$, $R^{1b}$ and $R^{1c}$ include lower alkyl having a carbon number of 1 to 6 which may have substituent(s) (e.g., methyl, ethyl, n-propyl, isopropyl, n-butyl, isobutyl, tert-butoxycarbonylmethyl, hydroxyethyl, phenylmethyl, carboxymethyl) and the like. Particularly, for example, $C_{1-6}$ alkyl such as methyl, ethyl, n-propyl, isopropyl, n-butyl, isobutyl and the like are preferable, methyl, ethyl, n-propyl and the like are more preferable, and ethyl and the like are particularly preferable.

As the "aromatic hydrocarbon group" of the "aromatic hydrocarbon group optionally having substituent(s)" for R, an aromatic hydrocarbon group having a carbon number of 6 to 14 (e.g., phenyl, naphthyl, anthryl, indenyl) and the like are preferable. In particular, for example, aryl having a carbon number of 6 to 10 (e.g., phenyl, naphthyl) and the like are preferable, and of these, phenyl and the like are particularly preferable.

As the "substituent" of the "aromatic hydrocarbon group optionally having substituent(s)" for R,
(1) a halogen atom (e.g., a fluorine atom, a chlorine atom, a bromine atom, an iodine atom),
(2) lower ($C_{1-4}$) alkyl (e.g., methyl, ethyl, propyl, butyl),
(3) lower ($C_{1-4}$) alkoxy (e.g., methoxy, ethoxy, propoxy, butoxy),
(4) lower ($C_{1-4}$) alkoxy-carbonyl (e.g., methoxycarbonyl, ethoxycarbonyl, propoxycarbonyl, butoxycarbonyl),
(5) carboxy,
(6) nitro,
(7) cyano,
(8) hydroxy,
(9) acylamino (e.g., alkanoylamino having a carbon number of 1 to 4 such as acetylamino, propionylamino, butyrylamino and the like),
(10) cycloalkyl having a carbon number of 3 to 6 (e.g., cyclopropyl, cyclopentyl),
(11) aryl having a carbon number of 6 to 10 (e.g., phenyl, naphthyl, indenyl),
(12) halogeno lower ($C_{1-4}$) alkyl (e.g., trifluoromethyl, trifluoroethyl),
(13) halogeno lower ($C_{1-4}$) alkoxy (e.g., trifluoromethoxy, 1,1,2,2-tetrafluoroethoxy, 2,2,3,3,3-pentafluoropropoxy),
(14) lower ($C_{1-4}$) alkylthio (e.g., methylthio, ethylthio, propylthio),
(15) lower ($C_{1-4}$) alkanesulfonyl (e.g., methanesulfonyl, ethanesulfonyl, propanesulfonyl),
(16) lower ($C_{1-4}$) alkanoyl (e.g., formyl, acetyl, propionyl),
(17) a 5-membered aromatic heterocyclic group (e.g., 1,2,3-triazolyl, 1,2,4-triazolyl, tetrazolyl, thiazolyl, isothiazolyl, oxazolyl, isoxazolyl, thiadiazolyl, thienyl, furyl),
(18) carbamoyl, lower ($C_{1-4}$) alkyl-carbamoyl (e.g., methylcarbamoyl, dimethylcarbamoyl, propylcarbamoyl),
(19) lower ($C_{1-4}$) alkoxy-carbonyl-lower ($C_{1-4}$) alkyl-carbamoyl (e.g., butoxycarbonylmethylcarbamoyl, ethoxycarbonylmethylcarbamoyl),
(20) 1,3-diacylguanidino-lower ($C_{1-4}$) alkyl (e.g., 1,3-diacetylguanidinomethyl, 1,3-bis-(tert-butoxycarbonyl)guanidinomethyl) and the like are used. Preferably, a halogen atom (e.g., a fluorine atom, a chlorine atom, a bromine atom, an iodine atom), lower ($C_{1-4}$) alkyl (e.g., methyl, ethyl, propyl, butyl) and the like are used. More preferably, a fluorine atom, a chlorine atom and methyl are used.

These substituents substitute at substitutable positions of the aromatic hydrocarbon group, and the number of the substituents is preferably 1 to 5, more preferably 1 to 3, most preferably 1 or 2. When two or more of such substituents are present, they may be the same or different.

The "heterocyclic group" of the "heterocyclic group optionally having substituent(s)" for R is, for example, a 5 to 8-membered ring (particularly a 5 or 6-membered ring) group containing 1 to several, preferably 1 to 4, hetero atoms such as nitrogen atom (optionally oxidized), oxygen atom, sulfur atom and the like, and a fused ring group thereof. As such heterocyclic group, pyrrolyl, pyrazolyl, imidazolyl, 1,2,3-triazolyl, 1,2,4-triazolyl, furyl, thienyl, oxazolyl, isoxazolyl, 1,2,3-oxadiazolyl, 1,2,4-oxadiazolyl, 1,2,5-oxadiazolyl, 1,3,4-oxadiazolyl, thiazolyl, isothiazolyl, 1,2,3-thiadiazolyl, 1,2,4-thiadiazolyl, 1,2,5-thiadiazolyl, 1,3,4-thiadiazolyl, pyridyl, pyridazinyl, pyrimidinyl, pyrazinyl, indolyl, pyranyl, thiopyranyl, dioxinyl, dioxolyl, quinolyl, pyrido[2,3-d]pyrimidyl, 1,5-, 1,6-, 1,7-, 1,8-, 2,6- or 2,7-naphthyridyl, thieno[2,3-d]pyridyl, benzopyranyl, tetrahydrofuryl, tetrahydropyranyl, dioxolanyl, dioxanyl and the like are used.

These heterocyclic groups are optionally substituted by 1 to 3 substituents selected from $C_{1-4}$ alkyl (e.g., methyl, ethyl), hydroxy, oxo, $C_{1-4}$ alkoxy (e.g., methoxy, ethoxy) and the like at substitutable positions. When two or more substituents are present, they may be the same or different.

Preferable examples of the above-mentioned "aliphatic hydrocarbon group" for $R^0$ or $R^2$ include lower alkyl having a carbon number of 1 to 6 (e.g., methyl, ethyl, n-propyl, isopropyl, n-butyl, isobutyl, tert-butoxycarbonylmethyl, hydroxyethyl) and the like. Of these, for example, $C_{1-6}$ alkyl such as methyl, ethyl, n-propyl, isopropyl, n-butyl, isobutyl and the like is preferable. For example, methyl, ethyl, n-propyl and the like are more preferable, and methyl and the like are particularly preferable.

As $R^0$ or $R^2$, in particular, a hydrogen atom and methyl are preferable.

As the "aromatic hydrocarbon group" of the "aromatic hydrocarbon group optionally having substituent(s)" for Ar, an aromatic hydrocarbon group having a carbon number of 6 to 14 (e.g., phenyl, naphthyl, anthryl, indenyl) and the like are preferable. In particular, for example, aryl having a carbon number of 6 to 10 (e.g., phenyl, naphthyl) and the like are preferable. Of these, phenyl and the like are particularly preferable.

As the "substituent" of the "aromatic hydrocarbon group optionally having substituent(s)" for Ar,
(1) a halogen atom (e.g., a fluorine atom, a chlorine atom, a bromine atom, an iodine atom),
(2) lower ($C_{1-4}$) alkyl (e.g., methyl, ethyl, propyl, isopropyl, butyl),
(3) lower ($C_{1-4}$) alkoxy (e.g., methoxy, ethoxy, propoxy, butoxy),
(4) lower ($C_{1-4}$) alkoxy-carbonyl (e.g., methoxycarbonyl, ethoxycarbonyl, propoxycarbonyl, butoxycarbonyl),
(5) carboxy,
(6) nitro,
(7) cyano,
(8) hydroxy,
(9) acylamino (e.g., alkanoylamino having a carbon number of 1 to 4 such as acetylamino, propionylamino, butyrylamino and the like),
(10) cycloalkyl having a carbon number of 3 to 6 (e.g., cyclopropyl, cyclopentyl),
(11) aryl having a carbon number of 6-10 (e.g., phenyl, naphthyl, indenyl),
(12) halogeno lower ($C_{1-4}$) alkyl (e.g., trifluoromethyl, trifluoroethyl),
(13) halogeno lower ($C_{1-4}$) alkoxy (e.g., trifluoromethoxy, 1,1,2,2-tetrafluoroethoxy, 2,2,3,3,3-pentafluoropropoxy),
(14) lower ($C_{1-4}$) alkylthio (e.g., methylthio, ethylthio, propylthio),
(15) lower ($C_{1-4}$) alkanesulfonyl (e.g., methanesulfonyl, ethanesulfonyl, propanesulfonyl),
(16) lower ($C_{1-4}$) alkanoyl (e.g., formyl, acetyl, propionyl),
(17) a 5-membered aromatic heterocyclic group (e.g., 1,2,3-triazolyl, 1,2,4-triazolyl, tetrazolyl, thiazolyl, isothiazolyl, oxazolyl, isoxazolyl, thiadiazolyl, thienyl, furyl),
(18) carbamoyl,
(19) lower ($C_{1-4}$) alkyl-carbamoyl (e.g., methylcarbamoyl, dimethylcarbamoyl, propionylcarbamoyl),
(20) lower ($C_{1-4}$) alkoxy-carbonyl-lower ($C_{1-4}$) alkyl-carbamoyl (e.g., butoxycarbonylmethylcarbamoyl, tert-butoxycarbonylmethylcarbamoyl, ethoxycarbonylmethylcarbamoyl),
(21) 1,3-diacylguanidino-lower ($C_{1-4}$) alkyl (e.g., 1,3-diacetylguanidinomethyl, 1,3-bis-(tert-butoxycarbonyl)guanidinomethyl)
and the like are used. Preferably, a halogen atom (e.g., a fluorine atom, a chlorine atom, a bromine atom, an iodine atom), lower ($C_{1-4}$) alkyl (e.g., methyl, ethyl, propyl, butyl) and the like are used. More preferably, a fluorine atom, a chlorine atom and methyl are used.

These substituents substitute at substitutable positions of the aromatic hydrocarbon group, and the number of the substituents is preferably 1 to 5, more preferably 1 to 3, most preferably 1 or 2. When two or more of such substituents are present, they may be the same or different.

As Ar, specifically for example, phenyl, halogenophenyl, lower ($C_{1-4}$) alkylphenyl, lower ($C_{1-4}$) alkoxyphenyl, lower ($C_{1-4}$) alkoxy-carbonylphenyl, carboxyphenyl, nitrophenyl, cyanophenyl, halogeno lower ($C_{1-4}$) alkylphenyl, halogeno lower ($C_{1-4}$) alkoxyphenyl, lower ($C_{1-4}$) alkanoylphenyl, phenyl substituted by a 5-membered aromatic heterocyclic group, lower ($C_{1-4}$) alkoxy-carbonyl-lower ($C_{1-4}$) alkyl-carbamoylphenyl, 1,3-diacylguanidino-lower ($C_{1-4}$) alkylphenyl, phenyl substituted by a halogen atom and lower ($C_{1-4}$) alkyl, phenyl substituted by a halogen atom and lower ($C_{1-4}$) alkoxy-carbonyl, phenyl substituted by a halogen atom and cyano, phenyl substituted by a halogen atom and 5-membered aromatic heterocycle, phenyl substituted by a halogen atom and lower ($C_{1-4}$) alkoxy-carbonyl-lower ($C_{1-4}$) alkyl-carbamoyl and the like are used.

As Ar, phenyl optionally having substituent(s) is preferable. Particularly, halogenophenyl, lower ($C_{1-4}$) alkylphenyl, phenyl substituted by a halogen atom and lower ($C_{1-4}$) alkoxycarbonyl, phenyl substituted by a halogen atom and lower ($C_{1-4}$) alkyl and the like are preferably used.

As Ar, a group represented by the formula:

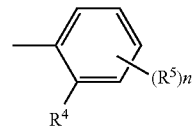

wherein $R^4$ and $R^5$ are the same or different and each is a halogen atom or lower ($C_{1-4}$) alkyl, and n is an integer of 0 to 2, is more preferable, and one wherein at least one of $R^4$ and $R^5$ is a halogen atom is further preferable.

As the halogen atom for $R^4$ or $R^5$, a fluorine atom or a chlorine atom is preferable.

As halogenophenyl, for example, 2,3-difluorophenyl, 2,3-dichlorophenyl, 2,4-difluorophenyl, 2,4-dichlorophenyl, 2,5-difluorophenyl, 2,5-dichlorophenyl, 2,6-difluorophenyl, 2,6-dichlorophenyl, 3,4-difluorophenyl, 3,4-dichlorophenyl, 3,5-difluorophenyl, 3,5-dichlorophenyl, 2-fluorophenyl, 2-chlorophenyl, 3-fluorophenyl, 3-chlorophenyl, 4-fluorophenyl, 4-chlorophenyl, 4-chloro-2-fluorophenyl, 2-chloro-4-fluorophenyl, 4-bromo-2-fluorophenyl, 2,3,4-trifluorophenyl, 2,4,5-trifluorophenyl, 2,4,6-trifluorophenyl and the like are used.

As lower ($C_{1-4}$) alkylphenyl, for example, 2-ethylphenyl, 2,6-diisopropylphenyl and the like are preferably used. As lower ($C_{1-4}$) alkoxyphenyl, for example 4-methoxyphenyl and the like are preferably used.

As lower ($C_{1-4}$) alkoxy-carbonylphenyl, for example, 2-ethoxycarbonylphenyl, 2-methoxycarbonylphenyl, 4-methoxycarbonylphenyl and the like are preferably used. As halogeno lower ($C_{1-4}$) alkylphenyl, for example, 2-trifluoromethylphenyl and the like are preferably used. As halogeno lower ($C_{1-4}$) alkoxyphenyl, for example, 2-trifluoromethoxyphenyl, 4-(2,2,3,3,3-pentafluoropropoxy)phenyl and the like are preferably used.

As lower ($C_{1-4}$) alkanoylphenyl, for example, 2-acetylphenyl and the like are preferably used. As phenyl substituted by a 5-membered aromatic heterocyclic group, for example, 4-(2H-1,2,3-triazol-2-yl)phenyl, 4-(2H-tetrazol-2-yl)phenyl, 4-(1H-tetrazol-1-yl)phenyl, 4-(1H-1,2,3-triazol-1-yl)phenyl and the like are preferably used. As lower ($C_{1-4}$) alkoxy-carbonyl-lower ($C_{1-4}$) alkyl-carbamoylphenyl, for example, 4-(N-ethoxycarbonylmethylcarbamoyl)phenyl and the like are preferably used. As 1,3-diacylguanidino-lower ($C_{1-4}$) alkylphenyl, for example, 4-(1,3-bis-tert-butoxycarbonylguanidinomethyl)phenyl and the like are preferably used.

As phenyl substituted by a halogen atom and lower ($C_{1-4}$) alkyl, for example, 2-fluoro-4-methylphenyl, 2-chloro-4-methylphenyl, 4-fluoro-2-methylphenyl and the like are preferably used. As phenyl substituted by a halogen atom and lower ($C_{1-4}$) alkoxy-carbonyl, for example, 2-chloro-4-methoxycarbonylphenyl and the like are preferably used. As phenyl substituted by a halogen atom and cyano, 2-chloro-4-cyanophenyl and the like are preferably used. As phenyl substituted by a halogen atom and 5-membered aromatic heterocyclic group, for example, 2-fluoro-4-(1H-1,2,4-triazol-1-yl)phenyl and the like are preferably used. As phenyl substituted by a halogen atom and lower ($C_{1-4}$) alkoxy-carbonyl-lower ($C_{1-4}$) alkyl-carbamoyl, for example, 2-chloro-4-(N-tert-butoxycarbonylmethylcarbamoyl)phenyl, 2-chloro-4-(N-ethoxycarbonylmethylcarbamoyl)phenyl and the like are preferably used.

More specifically, as Ar in particular, phenyl, phenyl substituted by 1 to 3 (particularly 1 or 2) halogen atoms (when substituted by plural halogen atoms, these halogen atoms may be the same or different; e.g., 2,3-difluorophenyl, 2,3-dichlorophenyl, 2,4-difluorophenyl, 2,4-dichlorophenyl, 2,5-difluorophenyl, 2,5-dichlorophenyl, 2,6-difluorophenyl, 2,6-dichlorophenyl, 3,4-difluorophenyl, 3,4-dichlorophenyl, 3,5-difluorophenyl, 3,5-dichlorophenyl, 4-bromo-2-fluorophenyl, 2-fluorophenyl, 2-chlorophenyl, 3-fluorophenyl, 3-chlorophenyl, 4-fluorophenyl, 4-chlorophenyl, 2-fluoro-4-chlorophenyl, 2-chloro-4-fluorophenyl, 2,3,4-trifluorophenyl, 2,4,5-trifluorophenyl), phenyl substituted by a halogen atom and lower ($C_{1-4}$) alkyl (e.g., 2-chloro-4-methylphenyl, 4-fluoro-2-methylphenyl) and the like are preferable. Of these, phenyl substituted by 1 to 3 (particularly 1 or 2) halogen atoms (when substituted by plural halogen atoms, these halogen atoms may be the same or different; e.g., 2,3-dichlorophenyl, 2,4-difluorophenyl, 2,4-dichlorophenyl, 2,6-dichlorophenyl, 2-fluorophenyl, 2-chlorophenyl, 3-chlorophenyl, 2-chloro-4-fluorophenyl, 2,4,5-trifluorophenyl), phenyl substituted by a halogen atom and lower ($C_{1-4}$) alkyl (e.g., 2-chloro-4-methylphenyl, 4-fluoro-2-methylphenyl) and the like are preferable. Particularly, 2,4-difluorophenyl, 2-chlorophenyl, 2-chloro-4-fluorophenyl, 2-chloro-4-methylphenyl and the like are preferable, and 2,4-difluorophenyl, 2-chloro-4-fluorophenyl and the like are preferable.

In the present specification, ring $A^1$ is preferably cycloalkene optionally substituted by 1 to 4 substituents selected from
(i) an aliphatic hydrocarbon group optionally having substituent(s),
(ii) an aromatic hydrocarbon group optionally having substituent(s),
(iii) a group represented by the formula: —$OR^{11}$ wherein $R^{11}$ is a hydrogen atom or an aliphatic hydrocarbon group optionally having substituent(s), and
(iv) halogen atoms. Of these, cycloalkene optionally substituted by 1 to 4 substituents selected from
(i) an aliphatic hydrocarbon group optionally having substituent(s),
(ii) an aromatic hydrocarbon group optionally having substituent(s), and
(iv) halogen atoms are preferable.

These substituents (i) to (iv) substitute on substitutable carbon atoms in the ring $A^1$, and when the ring $A^1$ is substituted by two or more of such substituents, the substituents may be the same or different. A single carbon atom may be substituted by two substituents, and different carbon atoms may be substituted by two or more substituents.

As the "aliphatic hydrocarbon group optionally having substituent(s)" as the substituent on the ring $A^1$, for example, those similar to the "aliphatic hydrocarbon group optionally having substituent(s)" for R and the like described above may be used.

As the "aromatic hydrocarbon group optionally having substituent(s)" as the substituent on the ring $A^1$, for example, those similar to the "aromatic hydrocarbon group optionally having substituent(s)" for Ar described above may be used.

As the substituents for the ring $A^1$, 1 or 2 $C_{1-6}$ alkyl groups (e.g., methyl, tert-butyl), phenyl, a halogen atom (e.g., fluorine, chlorine, bromine, iodine atoms), etc. are preferably used. When two substituents are present, they may be the same or different.

As the integer of 1 to 4 for n, 1 to 3 is preferable, and 2 is particularly preferable.

As the compound represented by the formula (I), the compound represented by the formula (Ibb') is preferable, and the compound represented by the formula (Inn) is more preferable.

Furthermore, preferred as a compound represented by the formula (Ibb') or the formula (Inn) is that wherein $R^1$ is lower alkyl optionally having substituent(s) (more preferably $R^1$ is $C_{1-6}$ alkyl), $R^2$ is a hydrogen atom or lower ($C_{1-6}$) alkyl, Ar is phenyl optionally having substituent(s) (more preferably Ar is phenyl substituted by 1 or 2 halogen atoms), and n is 1, 2 or 3 (more preferably n is 2).

A group represented by the formula:

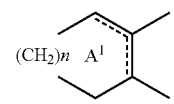

is a group represented by the formula:

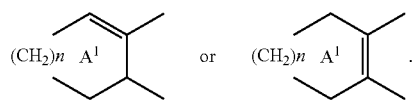

As the compound represented by the formula (I), for example, the following compounds and the like are preferable.

(1) A compound represented by the formula (Ia):

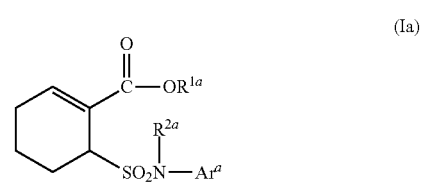

wherein $R^{1a}$ is $C_{1-6}$ alkyl, $R^{2a}$ is a hydrogen atom or $C_{1-6}$ alkyl, $Ar^a$ is phenyl substituted by 1 or 2 halogen atoms.

(2) compounds (1)-(85) described in Reference Example A mentioned below.

(3) the following compounds:

d-ethyl 6-[N-(2,4-difluorophenyl)sulfamoyl]-1-cyclohexene-1-carboxylate (compound 20), ethyl 6-[N-(2-chlorophenyl)sulfamoyl]-1-cyclohexene-1-carboxylate (compound 28), ethyl 6-[N-(2-chloro-4-methylphenyl)sulfamoyl]-1-cyclohexene-1-carboxylate (compound 45), and ethyl (6R)-6-[N-(2-chloro-4-fluorophenyl)sulfamoyl]-1-cyclohexene-1-carboxylate (compound 72).

The compound represented by the formula (II) is explained.

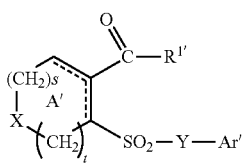

(II)

As the "aliphatic hydrocarbon group optionally having substituent(s)", "aromatic hydrocarbon group optionally having substituent(s)" and "heterocyclic group optionally having substituent(s)" for $R^{1'}$, those similar to these substituents for R can be used.

As the "aliphatic hydrocarbon group optionally having substituent(s)" for $R^{1b'}$ and $R^{1c'}$, for example, those similar to the aforementioned "aliphatic hydrocarbon group optionally having substituent(s)" for R can be used. As $R^{1b'}$ and $R^{1c'}$, for example, lower alkyl having 1 to 6 carbon atoms optionally having substituent(s) (e.g., methyl, ethyl, n-propyl, isopropyl, n-butyl, isobutyl, tert-butoxycarbonylmethyl, hydroxyethyl) and the like are preferably used. Of these, for example, methyl, ethyl, n-propyl, isopropyl, n-butyl, isobutyl and the like are preferably used. Particularly, for example, methyl, ethyl, n-propyl and the like are preferable, and ethyl and the like are specifically preferable.

As $R^{1'}$, a group represented by the formula: —$OR^{1a'}$ wherein $R^{1a'}$ is as defined above is preferable. As the "aliphatic hydrocarbon group optionally having substituent(s)" for $R^{1a'}$, for example, those similar to the "aliphatic hydrocarbon group optionally having substituent(s)" for the aforementioned R can be used. Lower alkyl having a carbon number of 1 to 6 which may have substituent(s) (e.g., methyl, ethyl, n-propyl, isopropyl, n-butyl, isobutyl, tert-butoxycarbonylmethyl, hydroxyethyl) and the like are preferably used. Of these, for example, $C_{1-6}$ alkyl such as methyl, ethyl, n-propyl, isopropyl, n-butyl, isobutyl and the like are preferably used. In particular, for example, methyl, ethyl, n-propyl and the like are preferable, and ethyl and the like are preferable.

As the "substituent" of the "methylene optionally having substituent(s)" for Y, for example, one or the same or different two substituents selected from (1) $C_{1-6}$ alkyl (e.g., methyl, ethyl, n-propyl, isopropyl, n-butyl, isobutyl), (2) hydroxyl substituted-$C_{1-6}$ alkyl (e.g., hydroxymethyl, hydroxyethyl), (3) $C_{1-4}$ alkoxy-carbonyl-$C_{1-4}$ alkyl (e.g., methoxycarbonylmethyl, ethoxycarbonylmethyl, tert-butoxycarbonylmethyl, methoxycarbonylethyl, ethoxycarbonylethyl, tert-butoxycarbonylethyl)

and the like are used, and of these, methyl is preferable. As Y, unsubstituted methylene is particularly preferable.

As the "substituent" of the "NH optionally having substituent(s)" for Y, (1) $C_{1-6}$ alkyl (e.g., methyl, ethyl, n-propyl, isopropyl, n-butyl, isobutyl), (2) hydroxyl substituted-$C_{1-6}$ alkyl (e.g., hydroxymethyl, hydroxyethyl), (3) $C_{1-4}$ alkoxy-carbonyl-$C_{1-4}$ alkyl (e.g., methoxycarbonylmethyl, ethoxycarbonylmethyl, tert-butoxycarbonylmethyl, methoxycarbonylethyl, ethoxycarbonylethyl, tert-butoxycarbonylethyl)

and the like are used, and of these, methyl is preferable. As Y, unsubstituted NH is particularly preferable.

In the "aromatic hydrocarbon group optionally having substituent(s)" for Ar', those similar to the aforementioned "aromatic hydrocarbon group optionally having substituent(s)" for Ar can be used.

Particularly, as Ar', those similar to Ar are preferable. Among others, a group represented by the formula (c):

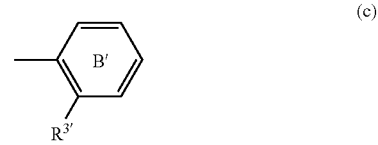

(c)

wherein $R^{3'}$ is a halogen atom or a lower alkyl group, and ring B' is optionally further substituted by 1 or 2 halogen atoms is preferable, and a group represented by the formula (c1):

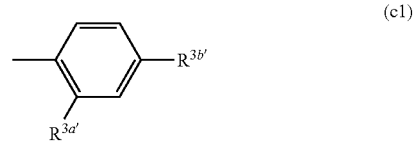

(c1)

wherein $R^{3a'}$ and $R^{3b'}$ are the same or different and each is a halogen atom is more preferable.

In the formula (c), a halogen atom for $R^{3'}$ and a halogen atom which is a substituent of ring B' and a halogen atom for $R^{3a'}$ and $R^{3b'}$ in the formula (c1), a fluorine atom or a chlorine atom is preferable. As the lower alkyl for $R^{3'}$ in the formula (c), for example, $C_{1-4}$ alkyl such as methyl, ethyl, propyl and the like can be mentioned. Among the groups represented by the formula (c), 2,4-difluorophenyl, 2-chloro-4-fluorophenyl, 2-methyl-4-chlorophenyl and the like are preferable. Among the groups represented by the formula (c1), 2,4-difluorophenyl, 2-chloro-4-fluorophenyl and the like are preferable.

X is methylene, NH, a sulfur atom or an oxygen atom, and methylene or an oxygen atom is particularly preferable.

Ring A' is a 5- to 8-membered ring substituted by a group represented by the formula: —CO—$R^{1'}$ wherein $R^{1'}$ is as defined above and a group represented by the formula: —$SO_2$—Y—Ar' wherein Y and Ar' are as defined above, and optionally further substituted by 1 to 4 substituents selected from the group consisting of (i) an aliphatic hydrocarbon group optionally having substituent(s), (ii) an aromatic hydrocarbon group optionally having substituent(s), (iii) a group represented by the formula: —$OR^{2'}$ wherein $R^{2'}$ is as defined above and (iv) a halogen atom. Of these, a 5- to 8-membered ring optionally substituted by 1 to 4 substituents selected from (i) an aliphatic hydrocarbon group optionally having substituent(s), (ii) an aromatic hydrocarbon group optionally having substituent(s) and (iv) a halogen atom are preferable.

These substituents are present at substitutable positions on the ring A'. When X constituting the ring is NH or methylene, they can substitute the NH and methylene. When ring A' is substituted by plural substituents, the kinds of such substituents may be the same or different. In addition, two substituents may substitute on the same carbon atom.

As the "aliphatic hydrocarbon group optionally having substituent(s)" and "aromatic hydrocarbon group optionally having substituent(s)", which are substituents of ring A', for example, those similar to the aforementioned group for R can be mentioned.

As the "aliphatic hydrocarbon group optionally having substituent(s)" for $R^{2'}$, for example, those similar to the aforementioned groups for R can be mentioned.

As the substituent for ring A', 1 or 2 $C_{1-6}$ alkyl (e.g., methyl, tert-butyl), phenyl, halogen atoms (e.g., fluorine, chlorine, bromine, iodine) and the like are preferably used. When two substituents are present, they may be the same or different.

The "s" is an integer of 0 to 2, "t" is an integer of 1 to 3, and the total of "s" and "t" is 4 or less, with preference given to "s" being 1 and "t" being 1.

A group represented by the formula:

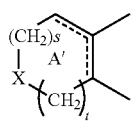
(b)

is a group represented by the formula:

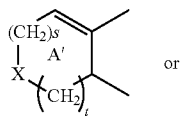
(b1)

or

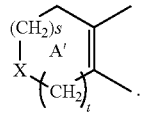
(b2)

As the compound represented by the formula (II), for example, the following compounds and the like are preferable.

(1) Compound (II) wherein $R^{1'}$ is a group represented by the formula: —$OR^{1a'}$ wherein $R^{1a'}$ is $C_{1-6}$ alkyl, a group represented by the formula:

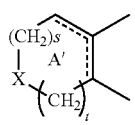
(b)

is a group represented by the formula:

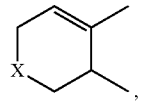
,

X is methylene or an oxygen atom,

Y is methylene or —NH—, and

Ar' is phenyl optionally having 1 or 2 substituents selected from a halogen atom and $C_{1-4}$ alkoxy, that is, a compound represented by the formula (IIa):

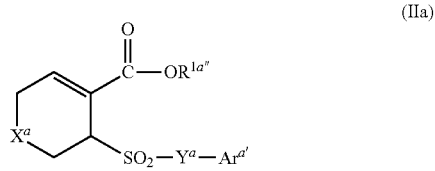
(IIa)

wherein $R^{1a''}$ is $C_{1-6}$ alkyl, $X^a$ is methylene or an oxygen atom, $Y^a$ is methylene or —NH—, $Ar^{a'}$ is phenyl optionally having 1 or 2 substituents selected from a halogen atom and $C_{1-4}$ alkoxy, provided when $X^a$ is methylene, then $Y^a$ is methylene optionally having substituent(s).

(2) Compound (II) wherein $R^{1'}$ is a group represented by the formula: —$OR^{1a'}$ ($R^{1a'}$ is $C_{1-6}$ alkyl), a group represented by the formula:

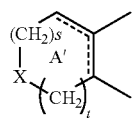
(b)

is a group represented by the formula:

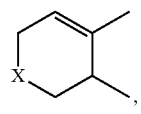
,

X and Y are both methylene, or X is an oxygen atom and Y is —NH—, and

Ar' is phenyl optionally having two halogen atoms (e.g., 2-chloro-4-fluorophenyl).

(3) Compounds (1')-(10') described in Reference Example B mentioned below.

(4) The following compounds:

ethyl 6-[(2-chloro-4-fluorobenzyl)sulfonyl]-1-cyclohexene-1-carboxylate (compound 4'), ethyl (+)-6-[(2-chloro-4-fluorobenzyl)sulfonyl]-1-cyclohexene-1-carboxylate (compound 6'), ethyl 3-[(2-chloro-4-fluorophenyl)sulfamoyl]-3,6-dihydro-2H-pyran-4-carboxylate (compound 8'), and ethyl (3S)-3-[N-(2-chloro-4-fluorophenyl)sulfamoyl]-3,6-dihydro-2H-pyran-4-carboxylate (compound 9').

A compound represented by the formula (III) is explained.

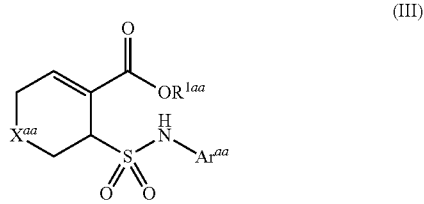

(III)

$R^{1aa}$ is $C_{1-6}$ alkyl (e.g., methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl etc.). Of these, ethyl is preferable.

$X^{aa}$ is methylene or an oxygen atom.

$Ar^{aa}$ is phenyl optionally having 1 or 2 substituents selected from a halogen atom (e.g., fluorine atom, chlorine atom, bromine atom, iodine atom etc.), $C_{1-6}$ alkyl (e.g., methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl, 2-ethylbutyl etc.) and $C_{1-6}$ alkoxy (e.g., methoxy, ethoxy, propoxy, isopropoxy, butoxy, isobutoxy, sec-butoxy, tert-butoxy, pentoxy, isopentoxy, hexoxy etc.). As $Ar^{aa}$, phenyl optionally having 1 or 2 substituents selected from a halogen atom (particularly, a fluorine atom, a chlorine atom) and $C_{1-6}$ alkyl (particularly, methyl, ethyl, isopropyl) is preferable. When two substituents are present, they may be the same or different.

As a compound represented by the formula (III), for example, the following compounds and the like are preferable.

(1) A compound wherein $R^{1aa}$ is ethyl,
$X^{aa}$ is methylene or an oxygen atom,
$Ar^{aa}$ is phenyl optionally having 1 or 2 substituents selected from a halogen atom (particularly, a fluorine atom, a chlorine atom) and $C_{1-6}$ alkyl (particularly, methyl, ethyl, isopropyl).

(2) Compounds 1, 3, 4, 6, 7, 10-17, 19, 20, 27-30, 34, 35, 37-39, 41, 45-47 and 71-74 of Reference Example A and compounds 7'-9' of Reference Example B.

(3) The following compounds:
d-ethyl 6-[N-(2,4-difluorophenyl)sulfamoyl]-1-cyclohexene-1-carboxylate (compound 20),
ethyl 6-[N-(2-chlorophenyl)sulfamoyl]-1-cyclohexene-1-carboxylate (compound 28),
ethyl 6-[N-(2-chloro-4-methylphenyl)sulfamoyl]-1-cyclohexene-1-carboxylate (compound 45),
ethyl (6R)-6-[N-(2-chloro-4-fluorophenyl)sulfamoyl]-1-cyclohexene-1-carboxylate (compound 72),
ethyl 3-[(2-chloro-4-fluorophenyl)sulfamoyl]-3,6-dihydro-2H-pyran-4-carboxylate (compound 8'),
ethyl (3S)-3-[N-(2-chloro-4-fluorophenyl)sulfamoyl]-3,6-dihydro-2H-pyran-4-carboxylate (compound 9').

(4) The following compounds:
ethyl (6R)-6-[N-(2-chloro-4-fluorophenyl)sulfamoyl]-1-cyclohexene-1-carboxylate (compound 72), and
ethyl (3S)-3-[N-(2-chloro-4-fluorophenyl)sulfamoyl]-3,6-dihydro-2H-pyran-4-carboxylate (compound 9').

(5) The following compound:
ethyl (6R)-6-[N-(2-chloro-4-fluorophenyl)sulfamoyl]-1-cyclohexene-1-carboxylate (compound 72).

(6) The following compound:
ethyl (3S)-3-[N-(2-chloro-4-fluorophenyl)sulfamoyl]-3,6-dihydro-2H-pyran-4-carboxylate (compound 9').

When the compounds represented by the formulas (I), (II) and (III) have stereoisomers, each stereoisomer and a mixture of these stereoisomers are both encompassed in the present invention.

Furthermore, when the compound represented by the formula (I) is a compound represented by the formula (Icc) or (Inn), and the formula (b) of the compound represented by the formula (II) is the formula (b1), s and t are 1 and the compound represented by the formula (III), each has an optical isomer based on the asymmetric carbon in cycloalkene or cyclohexene ring. Such optical isomer and a mixture of such optical isomers are both encompassed in the present invention.

The compounds represented by the formulas (I), (II) and (III) may be converted into a salt with an inorganic base, organic base, inorganic acid, organic acid, basic or acidic amino acid, and the like. As the salt with an inorganic base, for example, an alkali metal salt such as sodium and potassium salts, etc.; an alkaline earth metal salt such as calcium and magnesium salts, etc.; aluminum salt; ammonium salt; and the like are used. As the salt with an organic base, for example, a salt with trimethylamine, triethylamine, pyridine, picoline, ethanolamine, diethanolamine, triethanolamine, dicyclohexylamine, N,N'-dibenzylethylenediamine, etc can be used. As the salt with an inorganic acid, for example, a salt with hydrochloric acid, hydrobromic acid, nitric acid, sulfuric acid, phosphoric acid, etc can be used. As the salt with an organic acid, for example, a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like can be used. As the salt with a basic amino acid, for example, a salt with arginine, lysine, ornithine, etc can be used. As the salt with acidic amino acid, for example, a salt with aspartic acid, glutamic acid, and the like can be used.

A prodrug of the compound represented by the formula (I), (II) or (III) or a salt thereof is a compound which is converted into a parent compound (that is, the compound represented by the formula (I), (II) or (III)) as a result of a reaction with an enzyme, gastric acid etc. under physiological conditions in vivo. Thus, the compound is converted into a parent compound by enzymatical oxidation, reduction, hydrolysis etc., by hydrolysis due to gastric acid etc. A prodrug of a parent compound may be a compound obtained by subjecting an amino group of a parent compound to an acylation, alkylation or phosphorylation (e.g., a compound obtained by subjecting an amino group of a parent compound to an eicosanoylation, alanylation, pentylaminocarbonylation, 2-hydroxypropionylation, 2-acetoxypropionylation, (5-methyl-2-oxo-1,3-dioxolen-4-yl)methoxycarbonylation, tetrahydrofuranylation, pyrrolidylmethylation, pivaloyloxymethylation, tert-butylation, etc.); a compound obtained by subjecting a hydroxy group of a parent compound to an acylation, alkylation, phosphorylation or boration (e.g., a compound obtained by subjecting a hydroxy group of a parent compound to an acetylation, palmitoylation, propanoylation, pivaloylation, succinylation, fumarylation, alanylation, dimethylaminomethylcarbonylation, etc.); a compound obtained by subjecting a carboxyl group of a parent compound to an esterification or amidation (e.g., a compound obtained by subjecting a carboxyl group of a parent compound to an ethyl-esterification, phenyl-esterification, carboxymethyl-esterification, dimethylaminomethyl-esterification, pivaloyloxymethyl-esterification, ethoxycarbonyloxyethyl-esterification, phthalidyl-esterification, (5-methyl-2-oxo-1,3-dioxolen-4-yl)methyl-esterification, cyclohexyloxycarbonylethyl-esterification and methylamidation, etc.) and the like. Any of these compounds can be produced from a parent compound by a method known per se.

A prodrug of the compound represented by the formula (I), (II) or (III) may also be one which is converted into a parent compound (that is, the compound represented by the formula (I), (II) or (III)) under a physiological condition, such as those described in "IYAKUHIN no KAIHATSU (Development of Pharmaceuticals)", Vol. 7, Design of Molecules, p. 163-198, Published by HIROKAWA SHOTEN (1990).

The compound represented by the formula (I), a salt thereof or a prodrug thereof can be produced according to a method known per se, for example, a production method described in WO99/46242 and WO02/32859 or a method analogous thereto.

The compound represented by the formula (II), a salt thereof or a prodrug thereof can be produced according to a method known per se, for example, a production method described in WO01/10826 or a method analogous thereto.

A compound represented by the formula (III) or a salt thereof or a prodrug thereof can be produced according to a method known per se. For example, when $X^{aa}$ in the formula (III) is methylene, it can be produced by the production methods described in WO99/46242 and WO02/32859 or the method analogous thereto, and when $X^{aa}$ is an oxygen atom, it can be produced by the production methods described in WO01/10826, the below-mentioned Reference Example 1 and Reference Example 2 or a method analogous thereto.

When the optically active compound or a salt thereof contains an enantiomer, general separation means may be applied such as diastereomeric salt methods wherein a salt with an optically active acid (e.g., camphor sulfonic acid) or optically active base (e.g., 1-methylbenzylamine) is formed, inclusion compound methods using an optically active host molecule (e.g., 1,6-bis(2-chlorophenyl)-1,6-diphenylhexa-2,4-diyn-1,6-diol), various chromatographies (e.g., liquid chromatography using an optically active column), fractional recrystallization and the like, whereby an optically pure compound can be obtained.

A compound represented by the formula (I), (II) or (III), or a salt thereof or a prodrug thereof (hereinafter to be comprehensively referred to as "compound A") may be any of hydrate, non-hydrate, solvate and non-solvate.

In addition, compound A may be labeled with an isotope (e.g., $^3H$, $^{14}C$, $^{35}S$, $^{125}I$) and the like.

Furthermore, compound A may be a deuterated compound wherein $^1H$ is converted to $^2H(D)$.

Compound A is useful for suppressing (or mitigating) various neurological symptoms (e.g., dysesthesia such as numbness, pain (e.g., muscular pain, neuralgia), anesthesia, ache and the like) caused by peripheral nerve disorders that may be developed as the side effects of the administration of chemotherapeutic agents such as anti-cancer agent and the like.

Compound A is useful for the suppression (or mitigation) of numbness from among the above-mentioned neurological symptoms.

Compound A is also useful for the suppression (or mitigation) of pain from among the above-mentioned neurological symptoms.

Examples of the anti-cancer agent in the present specification include prophylactic agents and therapeutic agents for lung cancer (e.g., non-small cell lung cancer, small cell lung cancer, malignant mesothelioma), mesothelioma, pancreatic cancer (e.g., pancreatic duct cancer, pancreatic endocrine tumor), pharyngeal cancer, laryngeal cancer, esophagus cancer, gastric cancer (e.g., papillary adenocarcinoma, mucinous adenocarcinoma, adenosquamous carcinoma), duodenal cancer, small intestinal cancer, colorectal cancer (e.g., colorectal cancer, rectal cancer, anal cancer, familial colorectal cancer, hereditary nonpolyposis colorectal cancer, gastrointestinal stromal tumor), breast cancer (e.g., invasive ductal carcinoma, ductal carcinoma in situ, inflammatory breast cancer), ovarian cancer (e.g., ovarian epithelial carcinoma, extragonadal germ cell tumor, ovarian germ cell tumor, ovarian low malignant potential tumor), testis tumor, prostate cancer (e.g., hormone-dependent prostate cancer, non-hormone dependent prostate cancer), liver cancer (e.g., hepatocyte cancer, primary liver cancer, extrahepatic bile duct cancer), thyroid cancer (e.g., medullary thyroid carcinoma), kidney cancer (e.g., renal cell carcinoma, transitional cell carcinoma of renal pelvis and ureter), uterine cancer (e.g., uterine cervical cancer, cancer of uterine body, uterus sarcoma), brain tumor (e.g., medulloblastoma, glioma, pineal astrocytoma, pilocytic astrocytoma, diffuse astrocytoma, anaplastic astrocytoma, hypophysial adenoma), retina blastoma, skin cancer (e.g., basalioma, malignant melanoma), sarcoma (e.g., rhabdomyosarcoma, leiomyosarcoma, soft tissue sarcoma), malignant bone tumor, urinary bladder cancer, hematologic cancer (e.g., multiple myeloma, leukemia, malignant lymphoma, Hodgkin's disease, chronic bone marrow proliferative disease), cancer of unknown primary and the like, which cause peripheral nerve disorders as side effects.

Examples of such anti-cancer agent include taxane anti-cancer agents (e.g., paclitaxel (taxol), docetaxel), vinca alkaloid anti-cancer agents (e.g., vincristine, vinblastine), platinum preparations (e.g., cisplatin, carboplatin, oxaliplatin), molecular targeted drugs (e.g., bortezomib) and the like.

Among the above-mentioned anti-cancer agents, paclitaxel, vincristine, cisplatin, carboplatin and bortezomib are known as the agents having numbness and/or pain (e.g., muscular pain, neuralgia) as remarkable side effects (J. Clin Oncol. 24:1633-1642, 2006; Neurotoxicology, 27:992-1002, 2006; British Journal of Haematology, 127, 165-172, 2004).

Therefore, compound A is particularly useful for suppressing (or mitigating) dysesthesia such as numbness and/or pain (e.g., muscular pain, neuralgia) and the like caused by paclitaxel, vincristine, cisplatin, carboplatin and/or bortezomib. Particularly, compound A is useful for suppressing (or mitigating) dysesthesia such as numbness and/or pain (e.g., muscular pain, neuralgia) and the like caused by paclitaxel.

The dose of the aforementioned anti-cancer agents can be appropriately determined based on the clinical dose of each of the agents. As long as compound A can suppress the side effects, a dose higher than the conventional dose can also be administered.

In the case of paclitaxel as a representative example, the dose is administered by drip infusion according to the schedule of an administration at 60-70 mg/m$^2$ every 3 weeks, or at 210 mg/m$^2$ once a week for 3 weeks and one week cessation of the drug.

Such preparation can be produced by the method conventionally used in the technical field of preparations, for example, the method described in the Japanese Pharmacopoeia and the like.

The dose of compound A can be appropriately determined in consideration of the dose and dosing period of the above-mentioned anti-cancer agents, age, body weight and symptom of the subject of administration, dosage form, administration method and the like.

Representatively, the dose of compound A is, for example, generally 0.1-10 mg/kg/day, preferably 0.6-2.4 mg/kg/day, of compound A in a free form for an adult patient (body weight 60 kg). This mount is orally or parenterally administered in one to several portions (e.g., 1-3 portions) a day. It is needless to say that an amount smaller than the aforementioned dose may be sufficient or an administration beyond the above level may be necessary, since the dose changes under various conditions as mentioned above.

Compound A can be safely administered to mammals (e.g., human, mouse, rat, rabbit, dog, cat, bovine, horse, swine, monkey) orally or parenterally.

Examples of the dosage form of compound A include oral preparations such as tablet (including sugar-coated tablet, film-coated tablet, sublingual tablet, orally disintegrating tablet), capsule (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparation (e.g., dermal preparation, ointment), suppository (e.g., rectal suppository, vaginal suppository), pellet, nasal preparations, pulmonary preparation (inhalant), eye drop and the like. In addition, these preparations may be release control preparations (e.g., sustained-release microcapsule) such as immediate-release preparations, sustained-release preparations and the like. Such preparation can be produced by the method conventionally used in the technical field of preparations, for example, the method described in the Japanese Pharmacopoeia and the like.

Compound A is used in combination with the aforementioned anti-cancer agents to suppress (or mitigate) various neurological symptoms caused by peripheral nerve disorders that may be developed as the side effects of the administration of the aforementioned anti-cancer agents.

In one embodiment, the present invention relates to kit of parts for suppressing a peripheral nerve disorder induced by an anti-cancer agent comprising compound A and the anti-cancer agent.

In another embodiment, the present invention relates to a medicament comprising compound A and the anti-cancer agent.

Here, one or more kinds of the aforementioned anti-cancer agents may be combined. For example, in the case of paclitaxel, it may be combined with cisplatin and/or carboplatin and administered.

For combined use of compound A and the aforementioned anti-cancer agents, the timing of the administration of compound A and an anti-cancer agent is not particularly limited. Compound A (or a pharmaceutical composition thereof) and an anti-cancer agent (or a pharmaceutical composition thereof) may be administered to an administration subject simultaneously or in a staggered manner.

When one or more kinds of anti-cancer agents are administered, similarly, each of compound A (or a pharmaceutical composition thereof) and one or more kinds of anti-cancer agents (or a pharmaceutical composition thereof) may be administered to an administration subject simultaneously or in a staggered manner.

The mode of administration of compound A and an anti-cancer agent is not particularly limited as long as compound A and an anti-cancer agent are combined.

Examples of such administration mode include the following:

(1) administration of a single preparation obtained by simultaneously processing compound A (or a pharmaceutical composition thereof) and one or more kinds of anti-cancer agents (or a pharmaceutical composition thereof) (to be sometimes abbreviated as "the combination drug of the present invention"), (2) simultaneous administration of two or more kinds of preparations of compound A (or a pharmaceutical composition thereof) and one or more kinds of anti-cancer agents (or a pharmaceutical composition thereof), which preparations are separately produced, by the same administration route, (3) administration of two or more kinds of preparations of compound A (or a pharmaceutical composition thereof) and one or more kinds of anti-cancer agents (or a pharmaceutical composition thereof), which preparations are separately produced, by the same administration route in a staggered manner, (4) simultaneous administration of two or more kinds of preparations of compound A (or a pharmaceutical composition thereof) and one or more kinds of anti-cancer agents (or a pharmaceutical composition thereof), which preparations are separately produced, by different administration routes, (5) administration of two or more kinds of preparations of compound A (or a pharmaceutical composition thereof) and one or more kinds of anti-cancer agents (or a pharmaceutical composition thereof), which preparations are separately produced, by different administration routes in a staggered manner (e.g., administration in the order of compound A (or a pharmaceutical composition thereof) and an anti-cancer agent (or a pharmaceutical composition thereof), or in the reverse order) and the like.

The mixing ratio of compound A and the aforementioned anti-cancer agent in the combination drug of the present invention can be appropriately determined according to the subject of administration, administration route, disease and the like.

For example, the content of compound A in the combination agent of the present invention differs depending on the form of a preparation, and is usually from about 0.01 to 99.8% by weight, preferably from about 0.1 to 50% by weight, further preferably from about 0.5 to 20% by weight, based on total of the preparation.

The content of the anti-cancer agent in the combination agent of the present invention varies depending on the form of the preparation, and is usually from about 0.01 to 99.8% by weight, preferably from about 0.1 to 50% by weight, further preferably from about 0.5 to 20% by weight, based on the total of the preparation.

When one or more kinds of anti-cancer agents are administered, the content of each anti-cancer agent can be determined within the range of the above-mentioned content. Here, the mixing rate of the respective anti-cancer agents can be appropriately determined according to the administration subject, administration route, disease and the like.

The content of additives such as carrier in the combination agent of the present invention differs depending on the form of a preparation, and is usually from about 1 to 99.98% by weight, preferably from about 10 to 90% by weight, based on total of the preparation.

When compound A and an anti-cancer agent are independently prepared, the contents thereof may be the same as those mentioned above.

When compound A is administered to a human, it can be safely administered orally or parenterally as it is or in a mixture with an appropriate pharmacologically acceptable carrier, excipient and diluent, in a pharmaceutical composition such as an oral administration formulation (e.g., powder, granule, tablet, capsule etc.), a parenteral administration formulation (e.g., injection, external formulation (e.g., nasal administration formulation, percutaneous administration formulation etc.) and suppository (e.g., rectal suppository and vaginal suppository etc.).

Any of these formulations may be produced by any method known per se which is employed ordinarily for producing a pharmaceutical formulation. The amount of compound A to be incorporated into a formulation may vary depending on the dosage forms, and is preferably about 10 to 95% by weight in an oral administration formulation described above and about 0.001 to about 95% by weight in a parenteral administration formulation described above.

For example, compound A can be prepared into an aqueous injection together with a solubilizer (e.g., β-cyclodextrins etc.), a dispersant (e.g., Tween 80 (manufactured by ATLASPOWDER USA), HCO 60 (manufactured by NIKKO CHEMICALS), carboxymethylcellulose, sodium arginate etc.), a preservative (e.g., methyl paraben, propyl paraben, benzyl alcohol, chlorobutanol etc.), an isotonic agent (e.g., sodium chloride, glycerine, sorbitol, glucose etc.) and the like according to a conventional method, or into an oil-based injection by appropriately dissolving, suspending or emulsifying using a vegetable oil (e.g., olive oil, sesame oil, peanut oil, cottonseed oil, corn oil etc.) and propylene glycol and the like.

An oral administration formulation can be produced by, for example, compressing compound A together with an excipient (e.g., lactose, sucrose, starch etc.), a disintegrant (e.g., starch, calcium carbonate etc.), a binder (e.g., starch, gum arabic, carboxymethyl cellulose, polyvinyl pyrrolidone, hydroxypropyl cellulose etc.), a lubricant (e.g., talc, magnesium stearate, polyethylene glycol 6000 etc.), and the like, followed by, where necessary, a coating process known per se for the purpose of masking a taste, forming an enteric coat, or achieving a sustained release.

For such coating agent, for example, hydroxypropylmethyl cellulose, ethyl cellulose, hydroxymethyl cellulose, hydroxypropyl cellulose, polyoxyethylene glycol, Tween 80, Pluronic F68, cellulose acetate phthalate, hydroxypropylmethyl cellulose phthalate, hydroxymethyl cellulose acetate succinate, Eudragit (manufactured by ROHM, Germany, a copolymer of methacrylic acid and acrylic acid), a dye (e.g., titanium oxide, colcothar etc.) and the like may appropriately be used.

Compound A can also be employed as an external formulation in the form of a solid or semi-solid or a liquid.

For example, a solid external formulation may be compound A as it is or can be produced by mixing compound A with an excipient (e.g., glycol, mannitol, starch, microcrystalline cellulose etc.), a thickening agent (e.g., natural gums, cellulose derivatives, acrylic acid polymers etc.) which is then converted into a powder composition. A semi-solid external formulation may be produced by a standard method and preferably used in the form of an aqueous or oil-based gel or ointment. A liquid external formulation may be produced by a method employed for producing an injection formulation or an analogous method in the form of an oil-based or aqueous suspension.

The solid, semi-solid or liquid external formulation may be supplemented also with a pH modifier (e.g., carbonic acid, phosphoric acid, citric acid, hydrochloric acid, sodium hydroxide etc.), an antiseptic (e.g., p-oxybenzoate esters, chlorobutanol, benzalkonium chloride etc.) and the like, as appropriate. Typically, an ointment usually containing about 0.1 to about 100 mg of compound A per 1 g a vaseline or a lanolin etc. as a formulation base, can be used.

Compound A may be also formulated as an oil or aqueous, solid or semi-solid or liquid suppository. As an oil base in preparing suppository, for example, a higher fatty acid glyceride (e.g., cocoa butter, WITEPSOL (manufactured by DYNAMIT NOBEL) etc.), a middle fatty acid (e.g., MYGLYOL (manufactured by DYNAMIT NOBEL) etc.), a vegetable oil (e.g., sesame oil, soybean oil, cottonseed oil etc.) and the like are used as appropriate. An aqueous base may be, for example, polyethylene glycol or propylene glycol, and an aqueous gel base may be, for example, a natural gums, a cellulose derivative, a vinyl polymer, an acrylic polymer and the like.

In the present invention, compound A (particularly, ethyl (6R)-6-[N-(2-chloro-4-fluorophenyl)sulfamoyl]-1-cyclohexene-1-carboxylate (compound 72), and ethyl (3S)-3-[N-(2-chloro-4-fluorophenyl)sulfamoyl]-3,6-dihydro-2H-pyran-4-carboxylate (compound 9')) may be used as an emulsion composition (adjusted to pH about 3.7-about 5.5) containing the compound and a buffer (hereinafter to be abbreviated as emulsion composition A).

According to emulsion composition A, compound A can be effectively used as a component of a composition comprising an emulsifier.

Compound A may be in a liquid form or a solid form in an oil phase, and emulsion composition A is formed as an oil-in-water type (O/W type) or S/O/W type emulsion composition.

Emulsion composition A can be produced by, for example, using emulsifier.

Emulsion composition A is a composition comprising dispersion phase particles comprising an oil component, an emulsifier, and compound A, and water containing buffer wherein dispersion phase particles are dispersed. The dispersion phase particles mean a dispersion phase wherein one of two liquids immiscible in each other is present as fine particles in the other.

As the oil component, any pharmaceutically acceptable fats and oils generally used for the preparation of fat emulsions in the pharmaceutical technical field can be used. Examples of fats and oils include vegetable oil, partially hydrogenated vegetable oil, fats and oils obtained by transesterification reaction (single acid group glyceride (simple glyceride) or mixed acid group glyceride (mixed glyceride)), and middle chain fatty acid glycerol ester and the like.

The aforementioned fats and oils include fatty acid glycerol ester having a carbon number of about 6 to 30 (preferably about 6 to 22). Examples of the aforementioned fatty acid include saturated fatty acid such as caproic acid, caprylic acid, capric acid, lauric acid, myristic acid, palmitic acid, stearic acid, behenic acid and the like, unsaturated fatty acid such as palmitoleic acid, oleic acid, linoleic acid, arachidonic acid, eicosapentanoic acid, docosahexaenoic acid and the like.

Among vegetable oils, a preferable oil component contains, for example, vegetable oil such as soybean oil, cottonseed oil, rape seed oil, peanut oil, safflower oil, sesame oil, rice bran oil, corn germ oil, sunflower oil, poppy oil, olive oil and the like, and the like. Among these vegetable oils, soybean oil and the like are preferably used.

As fats and oils, a middle chain fatty acid triglyceride having a carbon number of about 6 to 14 (preferably about 8 to 12) can also be used. Preferable middle chain fatty acid glycerol ester includes, for example, caprylic/capric triglycerides such as "miglyol810", "miglyol 812" (both manufactured by Huls, available from Mitsuba Trading Co., Ltd.) and the like, caprylic acid triglycerides (glycerol tricaprylic acid ester) such as "Panacete 800" (manufactured by NOF Corporation) and the like, and the like.

The amount of the oil component in emulsion composition A to be used is, for example, about 1 to about 30 wt %, preferably about 2 to about 25 wt %, more preferably about 2.5 to about 22.5 wt %, of the whole composition.

As the aforementioned emulsifier, any pharmaceutically acceptable emulsifier can be used. Particularly, pharmaceutically acceptable phospholipids and non-ionic surfactants are preferable. The emulsifier can be used alone or as a mixture of two or more kinds thereof.

Phospholipid includes, for example, naturally occurring phospholipids (e.g., egg-yolk lecithin, soybean lecithin etc.), hydrogenated products thereof, or synthetically obtained phospholipids (e.g., phosphatidylcholine, phosphatidylethanolamines, phosphatidic acid, phosphatidylserine, phosphatidylinositol, phosphatidylglycerol etc.) and the like. Among these phospholipids, egg-yolk lecithin, soybean lecithin, and phosphatidyl choline derived from egg-yolk and soybean are preferable. A particularly preferable phospholipid is lecithin. Among synthetic phospholipids, anionic phospholipid is preferable. As the anionic synthetic phospholipid, anionic synthetic phospholipids such as dimyristoylphosphatidylglycerol, dipalmitoylphosphatidylglycerol, distearoylphosphatidylglycerol, dioleoylphosphatidylglycerol, oleoylpalmitoylphosphatidylglycerol, dioctanoylphosphatidic acid, didecanoylphosphatidic acid, dilauroylphosphatidic acid, dimyristoylphosphatidic acid, dipalmitoylphosphatidic acid, diheptadecanoylphosphatidic acid, distearoylphosphatidic acid, dioleoylphosphatidic acid, arachidonylstearoylphosphatidic acid, dipalmitoylphosphatidylserine, dioleoylphosphatidylserine, dimyristoylphosphatidylinositol, dipalmitoylphosphatidylinositol, distearoylphosphatidylinositol, dioleoylphosphatidylinositol, dimyristoylphosphatidylserine, distearoylphosphatidylserine and the like are specifically used, and dimyristoylphosphatidylglycerol is particularly preferable.

These anionic synthetic phospholipids can be chemically synthesized by a method known per se, or can also be obtained by purification.

As the non-ionic surfactant, a polymer surfactant having a molecular weight of about 800 to 20000, for example, polyoxyethylene-polyoxypropylene copolymer, polyoxyethylene alkyl ether, polyoxyethylene alkyl aryl ether, hydrogenated castor oil polyoxyethylene derivative, sorbitan polyoxyethylene derivative, polyoxyethylene sorbitol derivative, polyoxyethylene alkyl ether sulfate and the like can be mentioned.

The emulsifiers of phospholipid and non-ionic surfactants can be used alone or as a mixture of two or more kinds thereof. Alternatively, commercially available phospholipids may be used.

The total amount of the emulsifier in emulsion composition A to be used is generally about 0.1 to about 10% (W/V), preferably about 0.2 to about 7% (W/V), more preferably about 0.5 to about 5% (W/V), relative to the whole composition. The anionic synthetic phospholipid is in a proportion of about 0.0001 to about 5% (W/V) relative to the whole composition.

In emulsion composition A, the proportion of the emulsifier relative to the oil component is, for example, about 0.1 to about 150 wt %, preferably about 0.5 to about 125 wt %, more preferably about 1 to about 100 wt %. The emulsifier is often used in a proportion of generally about 1 to about 15 wt %, particularly about 1 to about 10 wt %, relative to the oil component.

Water to be used in emulsion composition A is not particularly limited as long as it is acceptable as a pharmaceutical product and, for example, purified water, water for injection (distilled water for injection) and the like can be mentioned. For production of a product other than pharmaceutical products, water is not particularly limited.

The amount of water in emulsion composition A to be used is generally about 40 to about 99% (W/V), preferably about 55 to about 98.8% (W/V), relative to the whole composition.

Emulsion composition A can be prepared by mixing a dispersion phase component comprising compound A (main drug), an oil component and an emulsifier with water and emulsifying the mixture and a buffer may be added to an aqueous phase before emulsification, or may be added to the emulsion composition after emulsification. Where necessary, additives such as a stabilizer to improve the stability of the aforementioned main drug, an isotonicity agent to control the osmotic pressure, an emulsion aid to improve the emulsifying power, an emulsion stabilizer to improve stability of emulsifier and the like may be added.

Examples of the stabilizer include antioxidants (e.g., ascorbic acid, tocopherol, sorbic acid, retinol etc.), chelating agents (e.g., edetic acid, citric acid, tartaric acid etc., and salts thereof) and the like. The amount of the stabilizer to be used is generally about 0.00001 to about 10% (W/V), preferably about 0.0001 to about 5% (W/V), relative to the whole emulsion composition A.

An isotonicity agent contains, for example, glycerol, sugar alcohol, monosaccharides, disaccharides, amino acid, dextran, albumin and the like. These isotonicity agents can be used alone or in a mixture of two or more kinds thereof.

Examples of the emulsion aid include fatty acid having a carbon number of about 6 to 30, salts of such fatty acid, monoglycerides of the aforementioned fatty acid and the like. The aforementioned fatty acid includes, for example, caproic acid, capric acid, caprylic acid, lauric acid, myristic acid, palmitic acid, stearic acid, behenic acid, palmitoleic acid, oleic acid, linoleic acid, arachidonic acid, eicosapentanoic acid, docosahexaenoic acid and the like, and salts of fatty acid include, for example, alkali metal salts such as sodium salt, potassium salt and the like, calcium salt and the like.

As the emulsion stabilizer, for example, cholesterol, cholesteryl ester, tocopherol, albumin, fatty acid amide derivative, polysaccharides, fatty acid ester derivative of polysaccharides and the like can be used.

While the concentration of compound A in emulsion composition A varies depending on the pharmacological activity or blood kinetics of the compound, it is generally about 0.001 to about 5% (W/V), preferably about 0.01 to about 2% (W/V), more preferably about 0.1 to about 1.5% (W/V). In addition, the content of compound A in emulsion composition A can also be set to about 1 to about 5000 mg, preferably about 10 to about 2000 mg, more preferably about 100 to about 1500 mg, in 100 ml of the composition. In addition, the content of compound A can also be adjusted to about 0.001 to about 95 wt %, preferably about 0.01 to about 30 wt %, more preferably about 0.1 to about 3 wt %, relative to the whole composition.

The proportion (wt %) of compound A relative to the dispersion phase consisting of an oil component and an emulsifier is generally about 0.0047 to about 24%, preferably about 0.047 to about 9.4%.

Emulsion composition A is adjusted to pH about 3.7 to about 5.5, preferably about 3.7 to about 5.0, more preferably about 4.0 to about 5.0.

As a pH adjuster, for example, phosphoric acid, carbonic acid, citric acid, hydrochloric acid, sodium hydroxide and the like are used and hydrochloric acid, sodium hydroxide and the like are particularly preferable.

As the aforementioned buffer, any pharmaceutically acceptable buffer can be used. For example, a buffer containing acetic acid, glacial acetic acid, lactic acid, citric acid, phosphoric acid, carbonic acid, histidine, glycine, barbital, phthalic acid, adipic acid, ascorbic acid, maleic acid, succinic acid, tartaric acid, glutamic acid, benzoic acid, aspartic acid and a salt thereof (e.g., potassium, sodium etc.), specifically sodium acetate, sodium lactate, sodium citrate, disodium hydrogen phosphate, sodium dihydrogen phosphate, sodium carbonate, sodium hydrogen carbonate, hydrochloric acid, sodium hydroxide and the like as a constituent component is preferable. Moreover, respective buffers may be used in combination. Particularly, one or more buffers selected from acetate buffer, glacial acetate buffer, lactate buffer, citrate buffer and phosphate buffer are preferable.

As the buffer, (i) a combination of acetic acid or glacial acetic acid and sodium acetate (acetate buffer or glacial acetate buffer), or (ii) a combination of lactic acid and sodium lactate (lactate buffer), and the like are preferable.

The concentration of the buffer is generally not more than about 100 mM, specifically about 0.1 mM to about 100 mM, preferably about 0.2 mM to about 50 mM, more preferably about 5 mM to about 40 mM.

The pH adjuster is an acidic or alkaline compound to be added to adjust the pH of a solution to a desired pH.

The amount of the pH adjuster to be generally added to an injection is trace. The amount of sodium hydroxide as a pH adjuster in a fatty emulsion commercially available in Japan is often not more than about 0.5 mM. While the pH can be adjusted to a desired pH during preparing the solution, the pH of the solution easily changes by the addition of an acid or alkali, and maintenance of pH is difficult.

The buffer is a compound having an action to reduce changes in pH on addition of acid or alkali, namely, a bufferizing action. In many cases, it is a mixed solution of a weak acid and a salt thereof, or a weak base and a salt thereof.

By addition of a buffer, emulsion composition A is not influenced by the development of free fatty acid, and can maintain a constant pH of an emulsion composition during high-pressure vapor sterilization and long-term preservation.

The amount of the buffer to be used for general injections is the aim of bufferizing action. For example, the amount of an acetate buffer in a solution injection commercially available in Japan is about 0.2 mM to about 100 mM.

Emulsion composition A is preferably used, for example, as a composition for injection.

Emulsion composition A can be basically produced by a known method or a method according thereto. Particularly, while a conventionally used emulsion technique can be utilized for the emulsion, compound A is preferably dissolved or dispersed in advance in an oil component. To be precise, a composition containing an O/W type or S/O/W type emulsion can be produced by dispersing a mixture of dispersion phase (1) containing an oil component and an emulsifier, and compound A (2) in water. The buffer may be added to an aqueous phase before emulsification, or added to an emulsion after emulsification during production.

The more preferable method includes, for example, a method of preparing an oil-in-water type composition comprising homogenizing an unhomogeneous mixture of a mixture of the main drug, an oil component, an emulsifier and, where necessary, an additive such as isotonicity agent and the like, and water containing a buffer using an emulsifying machine to give a crude emulsion, adding water as necessary, further homogenizing the emulsion using the above-mentioned emulsifying machine, and removing large particles by a filtration means such as a filter and the like. The aforementioned mixture is often warmed to a temperature of, for example, about 30 to about 90° C., preferably about 40 to about 80° C., to dissolve or disperse the main drug. As the emulsifying machine to emulsify an unhomogeneous mixture of the aforementioned mixture and water, conventionally used apparatuses, for example, homogenizers such as a pressurization injection type homogenizer, ultrasonication homogenizer and the like, homomixers such as high-speed rotation type mixer and the like, and the like can be used. To remove large particles having a particle size of not less than about 5 μm, homogenized emulsion is often subjected to a filtration means such as a filter and the like.

In emulsion composition A, the particle size distribution of a dispersion phase, wherein compound A is dissolved, is, for example, often about 0.01 to about 7 μm, preferably about 0.02 to about 5 μm. From the aspects of the stability of the emulsion and distribution in the body after administration, the mean particle size of the dispersion phase particles, wherein compound A is dissolved, is for example, about 0.025 to about 0.7 μm, more preferably about 0.05 to about 0.4 μm.

The mean particle size used in the present specification means a mean particle size based on the volume distribution and measured by a laser diffraction particle size distribution measurement apparatus, with the laser diffraction•scattering method as a measurement principle.

Pyrogen can be removed from emulsion composition A by a method known per se.

Where necessary, after nitrogen gas substitution, emulsion composition A is sterilized and tightly sealed.

Since pH of emulsion composition A is adjusted to about 3.7 to about 5.5 by adding a buffer, pH of the composition and mean particle size of the dispersion phase particles hardly change even after sterilization by an autoclave etc. or after long-term preservation, and the composition is stable. Therefore, the stability of compound A and emulsion composition A is superior. Moreover, emulsion composition A is free of a visibly observed free oil drop even after sterilization by an autoclave etc. or after long-term preservation, and therefore, phase separation of dispersion phase particles and water wherein the dispersion phase particles are dispersed does not occur, and the composition is stable.

Furthermore, emulsion composition A can increase the concentration of compound A, and control the particle size of the dispersion phase particles. Thus, it can enhance retentivity in blood, blood vessel permeability and transitivity into inflammation site. Therefore, in vivo kinetics or distribution in the body of compound A can be improved and targeting becomes possible, as a result of which administration of an effective drug with suppressed side effects becomes possible. Accordingly, emulsion composition A is particularly useful for the treatment of a target disease by an intravenous administration.

Compound A can also be used in combination with other drugs that suppress side effects of the anti-cancer agents, such as antidepressants (e.g., amitriptyline, imipramine, clomipramine, desipramine, doxepin, nortriptyline, duloxetine, milnacipran, fluoxetine, paroxetine, sertraline, citalopram), anticonvulsants (e.g., carbamazepine, pregabalin, gabapentin, lamotrigine, phenyloin, valproic acid), antiphlogistic analgesics (e.g., loxoprofen sodium, naproxen, indomethacin, ketoprofen, ibuprofen, diclofenac, celecoxib, acetaminophen, acetylsalicylic acid), adrenal cortex hormones (e.g., dexamethasone, prednisone), narcotics (e.g., morphine, oxycodone, fentanyl, methadone, codeine, tramadol), local anesthetics (Mexiletine, tocamide, lidocaine), alpha-2-adrenergic agonist (clonidine), herbal medicines (e.g., goshajinkigan, kanzoto), vitamins and the like.

The administration period, dose and administration mode of compound A and other drugs that suppress side effects of the anti-cancer agents are not limited, and can be appropriately determined in consideration of the age, body weight and symptom of the administration subject, dosage form, administration method, kind of side effect, combination of drugs and the like.

EXAMPLES

The present invention is explained in detail in the following by referring to Reference Examples and Experimental Examples, which are not to be construed as limitative.

The $^1$H-NMR spectrum was measured using tetramethylsilane as the internal standard and a Varian Mercury 300 (300 MHz) or Varian Gemini 200 (200 MHz) spectrometer, and total δ value was shown in ppm. In mixed solvents, the numerical values shown in parentheses are volume mixing ratio of each solvent. Unless particularly specified, % means weight percent. The ratio of solvents in silica gel chromatography is a volume ratio of the solvents to be mixed.

High polar diastereomer means a diastereomer having a smaller Rf value when Rf values of normal phase thin layer chromatography under the same conditions (e.g., ethyl acetate/hexane and the like can be used as the solvent) are compared, and low polar diastereomer means a diastereomer having a larger Rf value.

The following compounds of Reference Example A can be produced according to the Examples of WO99/46242. In Reference Example A, an optically active compound can be produced according to the Examples of WO02/32859. For example, compound 72 can be produced according to Examples 1 and 2 or Examples 3 and 4 of WO02/32859.

Reference Example A (compound 1) ethyl 6-[N-(4-chloro-2-fluorophenyl)sulfamoyl]-1-cyclohexene-1-carboxylate
(compound 2) ethyl 6-[N-(4-chloro-2-fluorophenyl)-N-methylsulfamoyl]-1-cyclohexene-1-carboxylate
(compound 3) ethyl 6-[N-(2,4-difluorophenyl)sulfamoyl]-1-cyclohexene-1-carboxylate
(compound 4) ethyl 6-[N-(2,6-diisopropylphenyl)sulfamoyl]-1-cyclohexene-1-carboxylate
(compound 5) ethyl 6-[N-(4-nitrophenyl)sulfamoyl]-1-cyclohexene-1-carboxylate
(compound 6) ethyl 6-(N-phenylsulfamoyl)-1-cyclohexene-1-carboxylate
(compound 7) ethyl 2-(N-phenylsulfamoyl)-1-cyclohexene-1-carboxylate
(compound 8) ethyl 2-[N-(4-methoxyphenyl)sulfamoyl]-1-cyclohexene-1-carboxylate
(compound 9) ethyl 2-[N-(4-chloro-2-fluorophenyl)sulfamoyl]-1-cyclohexene-1-carboxylate
(compound 10) ethyl 6-[N-(2-fluorophenyl)sulfamoyl]-1-cyclohexene-1-carboxylate
(compound 11) ethyl 6-[N-(3-fluorophenyl)sulfamoyl]-1-cyclohexene-1-carboxylate
(compound 12) ethyl 6-[N-(4-fluorophenyl)sulfamoyl]-1-cyclohexene-1-carboxylate
(compound 13) ethyl 6-[N-(2,6-difluorophenyl)sulfamoyl]-1-cyclohexene-1-carboxylate
(compound 14) ethyl 6-[N-(2,3-difluorophenyl)sulfamoyl]-1-cyclohexene-1-carboxylate
(compound 15) ethyl 6-[N-(2,5-difluorophenyl)sulfamoyl]-1-cyclohexene-1-carboxylate
(compound 16) ethyl 6-[N-(3,4-difluorophenyl)sulfamoyl]-1-cyclohexene-1-carboxylate
(compound 17) ethyl 6-[N-(3,5-difluorophenyl)sulfamoyl]-1-cyclohexene-1-carboxylate
(compound 18) ethyl 2-[N-(4-fluorophenyl)sulfamoyl]-1-cyclohexene-1-carboxylate
(compound 19) 1-ethyl 6-[N-(2,4-difluorophenyl)sulfamoyl]-1-cyclohexene-1-carboxylate
(compound 20) d-ethyl 6-[N-(2,4-difluorophenyl)sulfamoyl]-1-cyclohexene-1-carboxylate
(compound 21) ethyl 6-[N-(2-ethoxycarbonylphenyl)sulfamoyl]-1-cyclohexene-1-carboxylate
(compound 22) methyl 6-[N-(2,4-difluorophenyl)sulfamoyl]-1-cyclohexene-1-carboxylate
(compound 23) propyl 6-[N-(2,4-difluorophenyl)sulfamoyl]-1-cyclohexene-1-carboxylate
(compound 24) methyl 6-[N-(4-chloro-2-fluorophenyl)sulfamoyl]-1-cyclohexene-1-carboxylate
(compound 25) isopropyl 6-[N-(2,4-difluorophenyl)sulfamoyl]-1-cyclohexene-1-carboxylate
(compound 26) ethyl 6-[N-(2-methoxycarbonylphenyl)sulfamoyl]-1-cyclohexene-1-carboxylate
(compound 27) ethyl 6-[N-(2-fluoro-4-methylphenyl)sulfamoyl]-1-cyclohexene-1-carboxylate
(compound 28) ethyl 6-[N-(2-chlorophenyl)sulfamoyl]-1-cyclohexene-1-carboxylate
(compound 29) ethyl 6-[N-(2-chloro-4-fluorophenyl)sulfamoyl]-1-cyclohexene-1-carboxylate
(compound 30) ethyl 6-[N-(4-chlorophenyl)sulfamoyl]-1-cyclohexene-1-carboxylate
(compound 31) ethyl 6-[N-(2,3,4-trifluorophenyl)sulfamoyl]-1-cyclohexene-1-carboxylate
(compound 32) isobutyl 6-[N-(2,4-difluorophenyl)sulfamoyl]-1-cyclohexene-1-carboxylate
(compound 33) butyl 6-[N-(2,4-difluorophenyl)sulfamoyl]-1-cyclohexene-1-carboxylate
(compound 34) ethyl 6-[N-(4-bromo-2-fluorophenyl)sulfamoyl]-1-cyclohexene-1-carboxylate
(compound 35) ethyl 6-[N-(2,4-dichlorophenyl)sulfamoyl]-1-cyclohexene-1-carboxylate
(compound 36) ethyl 6-[N-(2-acetoxyphenyl)sulfamoyl]-1-cyclohexene-1-carboxylate
(compound 37) ethyl 6-[N-(3-chlorophenyl)sulfamoyl]-1-cyclohexene-1-carboxylate
(compound 38) ethyl 6-[N-(2,3-dichlorophenyl)sulfamoyl]-1-cyclohexene-1-carboxylate
(compound 39) ethyl 6-[N-(2-ethylphenyl)sulfamoyl]-1-cyclohexene-1-carboxylate
(compound 40) ethyl 6-[N-[4-(2H-1,2,3-triazol-2-yl)phenyl]sulfamoyl]-1-cyclohexene-1-carboxylate
(compound 41) ethyl 6-[N-(2,5-dichlorophenyl)sulfamoyl]-1-cyclohexene-1-carboxylate
(compound 42) ethyl 6-[N-(2-trifluoromethoxyphenyl)sulfamoyl]-1-cyclohexene-1-carboxylate
(compound 43) ethyl 6-[N-(2,4,5-trifluorophenyl)sulfamoyl]-1-cyclohexene-1-carboxylate
(compound 44) ethyl 6-[N-[4-(2H-tetrazol-2-yl)phenyl]sulfamoyl]-1-cyclohexene-1-carboxylate
(compound 45) ethyl 6-[N-(2-chloro-4-methylphenyl)sulfamoyl]-1-cyclohexene-1-carboxylate
(compound 46) ethyl 6-[N-(4-fluoro-2-methylphenyl)sulfamoyl]-1-cyclohexene-1-carboxylate
(compound 47) ethyl 6-[N-(2,6-dichlorophenyl)sulfamoyl]-1-cyclohexene-1-carboxylate
(compound 48) ethyl 6-[N-[4-(1H-tetrazol-1-yl)phenyl]sulfamoyl]-1-cyclohexene-1-carboxylate
(compound 49) ethyl 6-[N-(4-(1H-1,2,3-triazol-1-yl)phenyl]sulfamoyl]-1-cyclohexene-1-carboxylate
(compound 50) ethyl 6-[N-(2-trifluoromethylphenyl)sulfamoyl]-1-cyclohexene-1-carboxylate (compound 51) ethyl 6-[N-(4-methoxycarbonylphenyl)sulfamoyl]-1-cyclohexene-1-carboxylate
(compound 52) benzyl 6-[N-(2,4-difluorophenyl)sulfamoyl]-1-cyclohexene-1-carboxylate
(compound 53) ethyl 6-[N-[4-[2,3-bis(tert-butoxycarbonyl)guanidinomethyl]phenyl]sulfamoyl]-1-cyclohexene-1-carboxylate
(compound 54) ethyl 6-[N-(2-chloro-4-methoxycarbonylphenyl)sulfamoyl]-1-cyclohexene-1-carboxylate
(compound 55) ethyl 6-[N-(2-chloro-4-cyanophenyl)sulfamoyl]-1-cyclohexene-1-carboxylate
(compound 56) 2-hydroxyethyl 6-[N-(2,4-difluorophenyl)sulfamoyl]-1-cyclohexene-1-carboxylate
(compound 57) ethyl 6-[N-[2-fluoro-4-(1H-1,2,4-triazol-1-yl)phenyl]sulfamoyl]-1-cyclohexene-1-carboxylate
(compound 58) ethyl 5-[N-(2,4-difluorophenyl)sulfamoyl]-1-cyclopentene-1-carboxylate
(compound 59) tert-butyl [6-[N-(2,4-difluorophenyl)sulfamoyl]-1-cyclohexen-1-yl]carbonyloxyacetate
(compound 60) [6-[N-(2,4-difluorophenyl)sulfamoyl]-1-cyclohexen-1-yl]carbonyloxyacetic acid
(compound 61) ethyl 7-[N-(2,4-difluorophenyl)sulfamoyl]-1-cycloheptene-1-carboxylate
(compound 62) ethyl 6-[N-[2-chloro-4-(N-tert-butoxycarbonylmethylcarbamoyl)phenyl]sulfamoyl]-1-cyclohexene-1-carboxylate
(compound 63) ethyl 6-[N-[2-chloro-4-(N-ethoxycarbonylmethylcarbamoyl)phenyl]sulfamoyl]-1-cyclohexene-1-carboxylate
(compound 64) ethyl 5-[N-(2-chloro-4-fluorophenyl)sulfamoyl]-1-cyclopentene-1-carboxylate
(compound 65) ethyl 7-[N-(2-chloro-4-fluorophenyl)sulfamoyl]-1-cycloheptene-1-carboxylate
(compound 66) ethyl 2-[N-(2,4-difluorophenyl)sulfamoyl]-1-cyclopentene-1-carboxylate
(compound 67) 2-(4-methoxyphenyl)-4,5,6,7-tetrahydro-1,2-benzisothiazol-3(2H)-one 1,1-dioxide
(compound 68) 2-(4-fluorophenyl)-4,5,6,7-tetrahydro-1,2-benzisothiazol-3(2H)-one 1,1-dioxide
(compound 69) 2-[4-(2,2,3,3,3-pentafluoropropoxy)phenyl]-4,5,6,7-tetrahydro-1,2-benzisothiazol-3(2H)-one 1,1-dioxide
(compound 70) 2-(2,4-difluorophenyl)-5,6,7,7a-tetrahydro-1,2-benzisothiazol-3(2H)-one 1,1-dioxide
(compound 71) ethyl (6S)-6-[(2-chloro-4-fluoroanilino)sulfonyl]-1-cyclohexene-1-carboxylate
(also referred to as "l-ethyl 6-[N-(2-chloro-4-fluorophenyl)sulfamoyl]-1-cyclohexene-1-carboxylate")
(compound 72) ethyl (6R)-6-[N-(2-chloro-4-fluorophenyl)sulfamoyl]-1-cyclohexene-1-carboxylate (also referred to as "ethyl (6R)-6-[(2-chloro-4-fluoroanilino)sulfonyl]-1-cyclohexene-1-carboxylate")
(compound 73) ethyl 6-[N-(2-bromo-4-fluorophenyl)sulfamoyl]-1-cyclohexene-1-carboxylate
(compound 74) ethyl 6-[N-(4-bromo-2-chlorophenyl)sulfamoyl]-1-cyclohexene-1-carboxylate
(compound 75) high polar diastereomer of ethyl 6-[N-(2,4-difluorophenyl)sulfamoyl]-3-phenyl-1-cyclohexene-1-carboxylate high polar diastereomer
(compound 76) low polar diastereomer of ethyl 6-[N-(2,4-difluorophenyl)sulfamoyl]-3-phenyl-1-cyclohexene-1-carboxylate
(compound 75) high polar diastereomer of ethyl 6-[N-(2,4-difluorophenyl)sulfamoyl]-3-phenyl-1-cyclohexene-1-carboxylate
(compound 76) low polar diastereomer of ethyl 6-[N-(2,4-difluorophenyl)sulfamoyl]-3-phenyl-1-cyclohexene-1-carboxylate
(compound 77) high polar diastereomer of ethyl 6-[N-(2-chloro-4-fluorophenyl)sulfamoyl]-3-phenyl-1-cyclohexene-1-carboxylate
(compound 78) low polar diastereomer of ethyl 6-[N-(2-chloro-4-fluorophenyl)sulfamoyl]-3-phenyl-1-cyclohexene-1-carboxylate
(compound 79) high polar diastereomer of ethyl 6-[N-(2,4-difluorophenyl)sulfamoyl]-3-tert-butyl-1-cyclohexene-1-carboxylate
(compound 80) low polar diastereomer of ethyl 6-[N-(2,4-difluorophenyl)sulfamoyl]-3-tert-butyl-1-cyclohexene-1-carboxylate
(compound 81) high polar diastereomer of ethyl 6-[N-(2-chloro-4-fluorophenyl)sulfamoyl]-3-tert-butyl-1-cyclohexene-1-carboxylate
(compound 82) low polar diastereomer of ethyl 6-[N-(2-chloro-4-fluorophenyl)sulfamoyl]-3-tert-butyl-1-cyclohexene-1-carboxylate
(compound 83) ethyl 6-[N-(2,4-difluorophenyl)sulfamoyl]-3,3-dimethyl-1-cyclohexene-1-carboxylate
(compound 84) ethyl 6-[N-(2-chloro-4-fluorophenyl)sulfamoyl]-3,3-dimethyl-1-cyclohexene-1-carboxylate
(compound 85) ethyl 3-bromo-6-[N-(2,4-difluorophenyl)sulfamoyl]-1-cyclohexene-1-carboxylate The chemical structural formulas of compounds 1-85 are shown in Table 1-Table 12.

TABLE 1

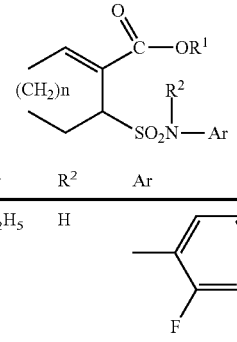

| Compound No. | $R^1$ | $R^2$ | Ar | n |
|---|---|---|---|---|
| 1 | $C_2H_5$ | H | 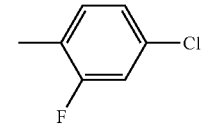 3-F, 4-Cl | 2 |
| 2 | $C_2H_5$ | $CH_3$ | 3-F, 4-Cl | 2 |
| 3 | $C_2H_5$ | H | 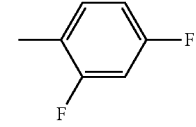 3-F, 4-F | 2 |
| 4 | $C_2H_5$ | H | 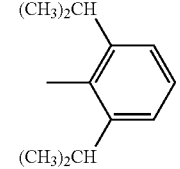 2-$(CH_3)_2CH$, 6-$(CH_3)_2CH$ | 2 |

TABLE 1-continued

[Structure:
$$\text{(CH}_2\text{)}_n\text{-CH(SO}_2\text{N(R}^2\text{)Ar)-C(=CHCH}_3\text{)-C(=O)-OR}^1$$ with ethyl branch]

| Compound No. | R¹ | R² | Ar | n |
|---|---|---|---|---|
| 5 | $C_2H_5$ | H | 4-$NO_2$-$C_6H_4$- | 2 |
| 6 | $C_2H_5$ | H | $C_6H_5$- | 2 |
| 10 | $C_2H_5$ | H | 2-F-$C_6H_4$- | 2 |

TABLE 2

| 11 | $C_2H_5$ | H | 3-F-$C_6H_4$- | 2 |
|---|---|---|---|---|
| 12 | $C_2H_5$ | H | 4-F-$C_6H_4$- | 2 |
| 13 | $C_2H_5$ | H | 2,6-F₂-$C_6H_3$- | 2 |
| 14 | $C_2H_5$ | H | 2,3-F₂-$C_6H_3$- | 2 |
| 15 | $C_2H_5$ | H | 2,4-F₂-$C_6H_3$- | 2 |
| 16 | $C_2H_5$ | H | 3,4-F₂-$C_6H_3$- | 2 |
| 17 | $C_2H_5$ | H | 3,5-F₂-$C_6H_3$- | 2 |
| 19 (l-form) | $C_2H_5$ | H | 2,4-F₂-$C_6H_3$- | 2 |
| 20 (d-form) | $C_2H_5$ | H | 2,4-F₂-$C_6H_3$- | 2 |

TABLE 3

| 21 | $C_2H_5$ | H | 2-($C_2H_5OC(=O)$)-$C_6H_4$- | 2 |
|---|---|---|---|---|
| 22 | $CH_3$ | H | 2,4-F₂-$C_6H_3$- | 2 |
| 23 | $(CH_2)_2CH_3$ | H | 2,4-F₂-$C_6H_3$- | 2 |
| 24 | $CH_3$ | H | 4-Cl-2-F-$C_6H_3$- | 2 |
| 25 | $CH(CH_3)_2$ | H | 2,4-F₂-$C_6H_3$- | 2 |
| 26 | $C_2H_5$ | H | 2-($CH_3OC(=O)$)-$C_6H_4$- | 2 |
| 27 | $C_2H_5$ | H | 3-F-4-$CH_3$-$C_6H_3$- | 2 |

TABLE 3-continued

| 28 | $C_2H_5$ | H | 2-Cl-phenyl | 2 |
| 29 | $C_2H_5$ | H | 2-Cl-4-F-phenyl | 2 |
| 30 | $C_2H_5$ | H | 4-Cl-phenyl | 2 |

TABLE 4

| 31 | $C_2H_5$ | H | 2,3-diF-4-F-phenyl (2,3,4-triF-phenyl) | 2 |
| 32 | $CH_2CH(CH_3)_2$ | H | 2,4-diF-phenyl | 2 |
| 33 | $(CH_2)_3CH_3$ | H | 2,4-diF-phenyl | 2 |
| 34 | $C_2H_5$ | H | 4-Br-2-F-phenyl | 2 |
| 35 | $C_2H_5$ | H | 2,4-diCl-phenyl | 2 |
| 36 | $C_2H_5$ | H | 2-(CH_3C(O))-phenyl | 2 |
| 37 | $C_2H_5$ | H | 3-Cl-phenyl | 2 |

TABLE 4-continued

| 38 | $C_2H_5$ | H | 2,3-diCl-phenyl | 2 |
| 39 | $C_2H_5$ | H | 2-$C_2H_5$-phenyl | 2 |
| 40 | $C_2H_5$ | H | 4-(2H-1,2,3-triazol-2-yl)-phenyl | 2 |

TABLE 5

| 41 | $C_2H_5$ | H | 2,5-diCl-phenyl | 2 |
| 42 | $C_2H_5$ | H | 2-$CF_3O$-phenyl | 2 |
| 43 | $C_2H_5$ | H | 2,4,5-triF-phenyl | 2 |
| 44 | $C_2H_5$ | H | 4-(2H-tetrazol-2-yl)-phenyl | 2 |
| 45 | $C_2H_5$ | H | 3-Cl-4-$CH_3$-phenyl | 2 |
| 46 | $C_2H_5$ | H | 4-F-3-$CH_3$-phenyl | 2 |

TABLE 5-continued
| 47 | C₂H₅ | H | 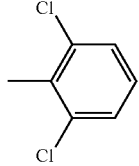 | 2 |
| 48 | C₂H₅ | H | 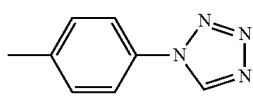 | 2 |
| 49 | C₂H₅ | H | 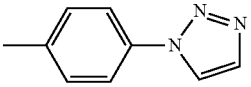 | 2 |
| 50 | C₂H₅ | H | 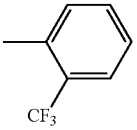 | 2 |
TABLE 6
| 51 | C₂H₅ | H | 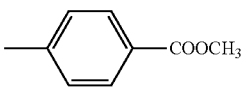 | 2 |
| 52 | CH₂-C₆H₅ | H | 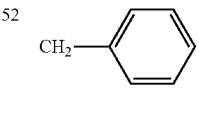 | 2 |
| 53 | C₂H₅ | H | 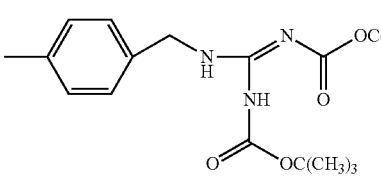 | 2 |
| 54 | C₂H₅ | H | 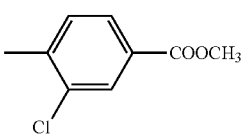 | 2 |
| 55 | C₂H₅ | H | 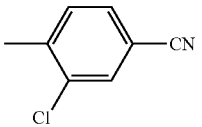 | 2 |
| 56 | (CH₂)₂OH | H | 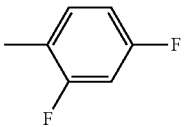 | 2 |
| 57 | C₂H₅ | H | 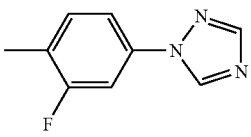 | 2 |
| 58 | C₂H₅ | H |  | 1 |
| 59 | CH₂COOC(CH₃)₃ | H | 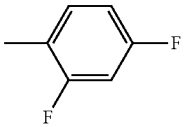 | 2 |

TABLE 6-continued

| 60 | CH₂COOH | H | 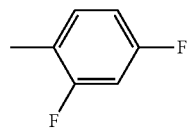 | | 2 |

TABLE 7

| 61 | C₂H₅ | H | (2,4-difluorophenyl) | 3 |
| 62 | C₂H₅ | H | (4-methyl-3-chlorophenyl)C(O)NHCH₂COOC(CH₃)₃ | 2 |
| 63 | C₂H₅ | H | (4-methyl-3-chlorophenyl)C(O)NHCH₂COOC₂H₅ | 2 |
| 64 | C₂H₅ | H | (2-chloro-4-fluorophenyl) | 1 |
| 65 | C₂H₅ | H | (2-chloro-4-fluorophenyl) | 3 |
| 71 (S-form) | C₂H₅ | H | (2-chloro-4-fluorophenyl) | 2 |
| 72 (R-form) | C₂H₅ | H | (2-chloro-4-fluorophenyl) | 2 |
| 73 | C₂H₅ | H | (2-bromo-4-fluorophenyl) | 2 |
| 74 | C₂H₅ | H | (3-chloro-4-bromophenyl) | 2 |

TABLE 8

Structure: ethyl 2-ethyl-3-(arylsulfamoyl)pent-2-enoate type with (CH₂)ₙ, OR¹, SO₂—NH—Ar

| Compound No. | R¹ | Ar | n |
|---|---|---|---|
| 7 | C₂H₅ | phenyl | 2 |
| 8 | C₂H₅ | 4-methoxyphenyl | 2 |
| 9 | C₂H₅ | 4-chloro-2-fluorophenyl | 2 |
| 18 | C₂H₅ | 4-fluorophenyl | 2 |
| 66 | C₂H₅ | 2,4-difluorophenyl | 1 |

TABLE 9

Structure: benzisothiazolinone-dione fused with cyclohexene, N—Ar

| Compound No. | | Ar |
|---|---|---|
| 67 | cyclohexenyl | 4-methoxyphenyl |
| 68 | cyclohexenyl | 4-fluorophenyl |

TABLE 9-continued

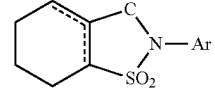

| Compound No. |  | Ar |
|---|---|---|
| 69 |  | —⟨⟩—OCH$_2$CF$_2$CF$_3$ |
| 70 |  | —⟨⟩ with F, F substituents |

TABLE 10

| Compound No. | R$^1$ | R$^2$ | R* | Ar |
|---|---|---|---|---|
| 75 high polar diastereomer | C$_2$H$_5$ | H | —⟨⟩ phenyl | —⟨⟩ 3,4-F,F |
| 76 low polar diastereomer | C$_2$H$_5$ | H | —⟨⟩ phenyl | —⟨⟩ 3,4-F,F |
| 77 high polar diastereomer | C$_2$H$_5$ | H | —⟨⟩ phenyl | —⟨⟩ 2-Cl,4-F |
| 78 low polar diastereomer | C$_2$H$_5$ | H | —⟨⟩ phenyl | —⟨⟩ 2-Cl,4-F |
| 79 high polar diastereomer | C$_2$H$_5$ | H | C(CH$_3$)$_3$ | —⟨⟩ 3,4-F,F |
| 80 low polar diastereomer | C$_2$H$_5$ | H | C(CH$_3$)$_3$ | —⟨⟩ 3,4-F,F |

TABLE 10-continued

| Compound No. | R$^1$ | R$^2$ | R* | Ar |
|---|---|---|---|---|
| 81 high polar diastereomer | C$_2$H$_5$ | H | C(CH$_3$)$_3$ |  |

TABLE 11

| 82 low polar diastereomer | C$_2$H$_5$ | H | C(CH$_3$)$_3$ |  |
| 85 | C$_2$H$_5$ | H | Br |  |

TABLE 12

| Compound No. | Ar |
|---|---|
| 83 |  |
| 84 |  |

Compounds 1'-8' of the following Reference Example B can be produced according to the Examples of WO01/10826. Compound 9' can be produced according to the following Reference Example 1 or Reference Example 2. Compound 10' can be produced according to the following Reference Example 1.

Reference Example B (compound 1') ethyl 6-(benzylsulfonyl)-1-cyclohexene-1-carboxylate
(compound 2') ethyl 6-[(4-methoxybenzyl)sulfonyl]-1-cyclohexene-1-carboxylate (compound 3') ethyl 6-[(2,4-difluorobenzyl)sulfonyl]-1-cyclohexene-1-carboxylate (compound 4') ethyl 6-[(2-chloro-4-fluorobenzyl)sulfonyl]-1-cyclohexene-1-carboxylate (compound 5') ethyl (−)-6-[(2-chloro-4-fluorobenzyl)sulfonyl]-1-cyclohexene-1-carboxylate (compound 6') ethyl (+)-6-[(2-chloro-4-fluorobenzyl)sulfonyl]-1-cyclohexene-1-carboxylate (compound 7') ethyl 3-[(2,4-difluorophenyl)sulfamoyl]-3,6-dihydro-2H-pyran-4-carboxylate (compound 8') ethyl 3-[(2-chloro-4-fluorophenyl)sulfamoyl]-3,6-dihydro-2H-pyran-4-carboxylate (compound 9') ethyl (3S)-3-[N-(2-chloro-4-fluorophenyl)sulfamoyl]-3,6-dihydro-2H-pyran-4-carboxylate (compound 10') ethyl (3R)-3-[N-(2-chloro-4-fluorophenyl)sulfamoyl]-3,6-dihydro-2H-pyran-4-carboxylate The chemical structural formulas of compounds 1'-10' are shown in Table 13 and Table 14.

TABLE 13

[Structure showing cyclohexene with C(=O)OCH₂CH₃ and SO₂—CH₂—Ar^a substituents]

| Compound No. | Ar^a |
|---|---|
| 1' | [phenyl] |
| 2' | [4-methoxyphenyl] |
| 3' | [2,4-difluorophenyl] |
| 4' | [2-chloro-4-fluorophenyl] |
| 5' (−)-form | [2-chloro-4-fluorophenyl] |
| 6' (+)-form | [2-chloro-4-fluorophenyl] |

TABLE 14

[Structure showing 3,6-dihydro-2H-pyran with C(=O)OCH₂CH₃ and SO₂—NH—Ar^a substituents]

| Compound No. | Ar^a |
|---|---|
| 7' | [2,4-difluorophenyl] |
| 8' | [2-chloro-4-fluorophenyl] |
| 9' (S-form) | [2-chloro-4-fluorophenyl] |
| 10' (R-form) | [2-chloro-4-fluorophenyl] |

Reference Example 1

Production of ethyl (3S)-3-[N-(2-chloro-4-fluorophenyl)sulfamoyl]-3,6-dihydro-2H-pyran-4-carboxylate (Reference Example B; compound 9') and ethyl (3R)-3-[N-(2-chloro-4-fluorophenyl)sulfamoyl]-3,6-dihydro-2H-pyran-4-carboxylate (Reference Example B; compound 10')

Ethyl 3-[N-(2-chloro-4-fluorophenyl)sulfamoyl]-3,6-dihydro-2H-pyran-4-carboxylate (Reference Example B; compound 8', 11.4 g) obtained according to Example 7 of WO01/10826 was resolved into two kinds of optical isomers by high performance liquid chromatography (CHIRALCEL OD; eluate: hexane/ethanol/trifluoroacetic acid=80/20/0.01) to give ethyl (3S)-3-[N-(2-chloro-4-fluorophenyl)sulfamoyl]-3,6-dihydro-2H-pyran-4-carboxylate (compound 9', 5.53 g) and ethyl (3R)-3-[N-(2-chloro-4-fluorophenyl)sulfamoyl]-3,6-dihydro-2H-pyran-4-carboxylate (compound 10', 5.59 g) each as an oil.

The above-mentioned compound 9' (4.07 g) was crystallized from a mixed solution of ethanol and hexane to give colorless powder crystals of compound 9' (3.78 g).

$^1$H-NMR (CDCl$_3$) δ: 1.30 (3H, t, J=7.2 Hz), 3.70 (1H, dd, J=13, 3.0 Hz), 4.21-4.50 (5H, m), 4.65 (1H, d, J=13 Hz), 6.92-7.15 (4H, m), 7.72 (1H, dd, J=9.3, 5.4 Hz).

elemental analysis value: C$_{14}$H$_{15}$ClFNO$_5$S
Calculated (%): C, 46.22; H, 4.16; N, 3.85.
Found (%): C, 46.18; H, 4.02; N, 3.87.
specific optical rotation: +94.3° (c=1.0, in methanol; 20° C.)

The above-mentioned compound 10' (5.59 g) was crystallized from a mixed solution of ethanol and hexane to give colorless powder crystals of compound 10' (5.34 g).

¹H-NMR (CDCl₃) δ: 1.30 (3H, t, J=7.0 Hz), 3.70 (1H, dd, J=13, 2.8 Hz), 4.19-4.48 (5H, m), 4.65 (1H, d, J=13 Hz), 6.92-7.16 (4H, m), 7.72 (1H, dd, J=9.2, 5.6 Hz).
elemental analysis value: C₁₄H₁₅ClFNO₅S
Calculated (%): C, 46.22; H, 4.16; N, 3.85.
Found (%): C, 46.19; H, 3.95; N, 3.84.
specific optical rotation: −96.0° (c=1.0, in methanol; 20° C.)

Reference Example 2

Production of ethyl (3S)-3-[N-(2-chloro-4-fluorophenyl)sulfamoyl]-3,6-dihydro-2H-pyran-4-carboxylate (Reference Example B; compound 9')

Production of ethyl 3-hydroxy-3,6-dihydro-2H-pyran-4-carboxylate

To an aqueous solution (400 mL) of (3R,4S)-tetrahydrofuran-3,4-diol (100 g) was added sodium periodate (225 g) at 0° C., and the mixture was stirred at room temperature for 1 hr. An aqueous solution (50 mL) of potassium carbonate (13.2 g) was added at room temperature, and an aqueous solution (100 mL) of ethyl diethylphosphonoacetate (322 g) was added dropwise over 2 hr. Then, an aqueous solution (800 mL) of potassium carbonate (384 g) was added dropwise over 2 hr. The reaction mixture was stirred at room temperature for 24 hr, and extracted with ethyl acetate. The extract was dried over anhydrous magnesium sulfate and the solvent was evaporated under reduced pressure. The residue was distilled under reduced pressure (110-130° C./3-4 mmHg). The obtained crude product was subjected to silica gel column chromatography (hexane/ethyl acetate=1:1) to give the title compound (66.5 g, 40%) as a colorless liquid.
¹H-NMR (CDCl₃) δ: 1.33 (3H, t, J=7.0 Hz), 2.85 (1H, J=5.0 Hz), 3.67-3.75 (1H, m), 3.91-3.98 (1H, m), 4.10-4.45 (5H, m), 7.07 (1H, d, J=2.6 Hz).

Production of ethyl (3R)-3-hydroxy-3,6-dihydro-2H-pyran-4-carboxylate

To a solution (380 mL) of ethyl 3-hydroxy-3,6-dihydro-2H-pyran-4-carboxylate (91.2 g) in diisopropyl ether were added vinyl hexanoate (150 mL) and Lipozyme IM (4.8 g). The reaction mixture was stirred at 35° C. for 24 hr and the insoluble material was filtered off. The obtained filtrate was concentrated under reduced pressure. The residue was subjected to silica gel column chromatography (hexane/ethyl acetate=6:1→1:1) to give the title compound (45.9 g, 50%).
¹H-NMR (CDCl₃) δ: 1.33 (3H, t, J=7.0 Hz), 2.85 (1H, J=5.0 Hz), 3.67-3.75 (1H, m), 3.91-3.98 (1H, m), 4.10-4.45 (5H, m), 7.07 (1H, d, J=2.6 Hz).
enantiomeric excess: >99% ee [column: CHIRALCEL OD (manufactured by DAICEL CHEMICAL INDUSTRIES, LTD.), mobile phase: hexane/2-propanol=95/5].

Production of ethyl (3S)-3-(acetylsulfanyl)-3,6-dihydro-2H-pyran-4-carboxylate

Under a nitrogen atmosphere, to a solution (500 mL) of ethyl (3R)-3-hydroxy-3,6-dihydro-2H-pyran-4-carboxylate (23.5 g) in tetrahydrofuran was added dropwise N,N-diisopropylethylamine (35.7 mL) at −70° C. Then, methanesulfonyl chloride (13.7 mL) was added dropwise, and the mixture was stirred at −45° C. for 2 hr. The mixture was again cooled to −70° C., N,N-diisopropylethylamine (14.6 mL) and thioacetic acid (35.7 mL) were respectively added, and the mixture was stirred at −45° C. for 2 hr. The reaction mixture was treated with 1N hydrochloric acid (300 mL) and extracted with diisopropyl ether (300 mL×2). The extract was washed with saturated aqueous sodium hydrogen carbonate solution (300 mL) and water (300 mL), dried over anhydrous magnesium sulfate, and concentrated under reduced pressure. The residue was subjected to silica gel column chromatography (hexane/ethyl acetate=6:1→4:1) to give the title compound (19.5 g, 62%).
¹H-NMR (CDCl₃) δ: 1.28 (3H, t, J=7.0 Hz), 2.34 (3H, s), 3.81-4.03 (2H, m), 4.10-4.52 (5H, m), 7.05-7.08 (1H, m).
enantiomeric excess: 98.0% ee [column: CHIRALCEL OD-H (manufactured by DAICEL CHEMICAL INDUSTRIES, LTD.), mobile phase: hexane/2-propanol=90/10].

Production of ethyl (3S)-3-sulfanyl-3,6-dihydro-2H-pyran-4-carboxylate

To a solution (100 mL) of ethyl (3S)-3-(acetylsulfanyl)-3,6-dihydro-2H-pyran-4-carboxylate (19.5 g) in ethanol was added dropwise hydrochloric acid-ethanol solution (24% w/w, 100 mL) at 0° C. The reaction mixture was stirred at room temperature for 40 hr, and cooled to 0° C. Saturated aqueous sodium hydrogen carbonate solution (750 mL) was added dropwise. The reaction mixture was maintained at 10° C. or lower, and the final pH was adjusted to 7 to 8. After extraction with ethyl acetate (500 mL×2), the extract was washed with water (300 mL×2), dried over anhydrous magnesium sulfate, and concentrated under reduced pressure. The residue was subjected to silica gel column chromatography (hexane/ethyl acetate=5:1) to give the title compound (14.5 g, 91%).
¹H-NMR (CDCl₃) δ: 1.32 (3H, t, J=7.2 Hz), 2.23 (1H, d, J=9.6 Hz), 3.64-4.48 (7H, m), 6.83-6.86 (1H, m). enantiomeric excess: 97.2% ee [column: CHIRALPAK AD (manufactured by DAICEL CHEMICAL INDUSTRIES, LTD.), mobile phase: hexane/2-propanol=98/2].

Production of ethyl (3S)-3-{[(2-chloro-4-fluorophenyl)amino]sulfanyl}-3,6-dihydro-2H-pyran-4-carboxylate To a solution (400 mL) of ethyl (3S)-3-sulfanyl-3,6-dihydro-2H-pyran-4-carboxylate (14.5 g) in dichloromethane was added dropwise tert-butyl hypochlorite (10 mL) at −78° C. After stirring for 30 min, 2-chloro-4-fluoroaniline (23 mL) was added dropwise at −78° C. The reaction mixture was stirred for 1 hr, and the reaction was discontinued with 5% aqueous sodium sulfite solution (300 mL). After extraction with dichloromethane (300 mL), the extract was washed with water, and dried over anhydrous magnesium sulfate. After concentration under reduced pressure, the residue was subjected to silica gel column chromatography (hexane/ethyl acetate=15:1→5:1) to give the title compound as a crude product (20.0 g, 96.3% ee). This product was crystallized from diisopropyl ether/hexane (120 mL, 1:5) to give the title compound (12.3 g, 62%) as white crystals.
¹H-NMR (CDCl₃) δ: 1.33 (3H, t, J=7.2 Hz), 3.72-3.79 (2H, m), 4.20-4.46 (5H, m), 5.53 (1H, br s), 6.90-7.03 (3H, m), 7.54-7.59 (1H, m).
enantiomeric excess: >99% ee [column: CHIRALPAK AD (manufactured by DAICEL CHEMICAL INDUSTRIES, LTD.), mobile phase: hexane/2-propanol=97.5/2.5].

Production of ethyl (3S)-3-[N-(2-chloro-4-fluorophenyl)sulfamoyl]-3,6-dihydro-2H-pyran-4-carboxylate (compound 9')

To a solution (200 mL) of ethyl (3S)-3-{[(2-chloro-4-fluorophenyl)amino]sulfanyl}-3,6-dihydro-2H-pyran-4-carboxylate (12.3 g) in ethyl acetate was added meta-chloroperbenzoic acid (24.5 g) at 0° C. After stirring at room temperature for 2 hr, the mixture was again cooled to 0° C., and 5% aqueous sodium sulfite solution (200 mL) and saturated aqueous sodium hydrogen carbonate solution (200 mL) were added dropwise. After extraction with ethyl acetate (200 mL×2), the extract was washed with saturated aqueous sodium hydrogen carbonate solution (200 mL) and water (200 mL), and dried over anhydrous magnesium sulfate. After concentration under reduced pressure, the residue was subjected to silica gel column chromatography (hexane/ethyl acetate=2:1) to give the title compound as a crude product (13.8 g). This product was crystallized from ethyl acetate/diisopropyl ether/hexane (115 mL, 5:100:10) to give the title compound (12.0 g, 90%).

$^1$H-NMR (CDCl$_3$) δ: 1.30 (3H, t, J=7.4 Hz), 3.66-3.74 (1H, m), 4.19-4.48 (5H, m), 4.65 (1H, d, J=12.8 Hz), 6.92-7.16 (4H, m), 7.68-7.75 (1H, m).

enantiomeric excess: >99% ee [column: CHIRALCEL OD (manufactured by DAICEL CHEMICAL INDUSTRIES, LTD.), mobile phase: hexane/ethanol/trifluoroacetic acid=80/20/0.1, flow rate: 0.5 mL/min, detection: UV 254 nm, temperature: 30° C.]

Experimental Example 1

Mice (C57BL/6N, male, 7-week-old) were divided into Group A (6 mice), Group B (6 mice), and Group C (6 mice). Group B and Group C were intraperitoneally administered with paclitaxel (dissolved in ethanol:Cremophor EL:saline=0.5:0.5:9; 4 mg/kg body weight). As Group A, non-treated animals were used. Group C was intravenously administered with compound 72 (10 mg/kg body weight) of Reference Example A dissolved in an emulsion containing soybean oil, egg-yolk lecithin, glycerol and the like immediately before and 1 and 2 weeks after intraperitoneal administration of paclitaxel (total 3 times). Thus, neither paclitaxel nor Compound 72 was administered to Group A; paclitaxel but not Compound 72 was administered to Group B; and both paclitaxel and Compound 72 were administered to Group C. Pain threshold of each group was measured 3 weeks after paclitaxel administration to Group B and Group C. Pain threshold is a weighed value (gram) at the time when a false escape response is observed by pressurizing the plantar part of the right hindlimb using a balance type pressing device (Ugo Basile). The results are shown in the following Table 15. The values in the Table show mean ±standard error of the weighed values.

TABLE 15

|         | Pain threshold (g) |
|---------|--------------------|
| Group A | 443.3 ± 32.8       |
| Group B | 185.0 ± 19.3       |
| Group C | 441.7 ± 28.6       |

From the above results, compound A has been shown to have a suppressing (or mitigating) action on neurological symptoms (e.g., dysesthesia such as numbness, pain and the like) of peripheral nerve disorders induced by paclitaxel.

Experimental Example 2

Mice (C57BL/6N, male, 8-week-old) were divided into Group A, Group B, and Group C. As Group A, non-treated animals were used. To Group B and Group C, any one of various anti- cancer agents (docetaxel, vincristine, cisplatin, carboplatin, bortezomib) is diluted with saline to a given concentration, and intraperitoneal administered (docetaxel at 3 mg/kg body weight, vincristine at 0.1 mg/kg body weight, cisplatin at 3 mg/kg body weight, carboplatin at 40 mg/kg body weight, bortezomib at 0.4 mg/kg body weight). Group C was intravenously administered with compound 72 (3 mg/kg body weight) of Reference Example A dissolved in an emulsion containing soybean oil, egg-yolk lecithin, glycerol and the like immediately before intraperitoneal administration of various anti-cancer agents. Thus, neither an enumerated anti-cancer agent nor Compound 72 was administered to Group A; an anti-cancer agent but not Compound 72 was administered to Groups B; and both an anti-cancer agent and Compound 72 were administered to Groups C. Pain threshold of each group was measured 1 week after the administration of the anti-cancer agent. Pain threshold is a weighed value (gram) at the time when a false escape response is observed by pressurizing the plantar part of the right hindlimb using a balance type pressing device (Ugo Basile). The results are shown in the following Table 16. The values in the Table show mean ±standard error of the weighed values, and n is the number of the mice in each group.

TABLE 16

| | Pain threshold (g) |
|---|---|
| non-treatment group | |
| Group A (n = 6) | 365.0 ± 17.8 |
| Docetaxel administration group | |
| Group B (n = 6) | 123.3 ± 8.0 |
| Group C (n = 6) | 276.7 ± 17.4** |
| Vincristine administration group | |
| Group B (n = 12) | 160.8 ± 16.0 |
| Group C (n = 12) | 289.2 ± 44.6** |
| Cisplatin administration group | |
| Group B (n = 12) | 118.3 ± 6.7 |
| Group C (n = 12) | 166.7 ± 18.5* |
| Carboplatin administration group | |
| Group B (n = 6) | 110.0 ± 6.8 |
| Group C (n = 6) | 213.3 ± 13.3** |
| Bortezomib administration group | |
| Group B (n = 6) | 126.7 ± 17.6 |
| Group C (n = 6) | 306.7 ± 24.0** |

*$p < 0.025$, **$p < 0.001$; t-test

From the above results, compound A has been shown to have a suppressing (or mitigating) action on neurological symptoms (e.g., dysesthesia such as numbness, pain and the like) of peripheral nerve disorders induced by various anti-cancer agents.

Experimental Example 3

Rat (Wistar, male, 5-week-old) were divided into Group A, Group B, and Group C. As Group A, non-treated animals were used. To Group B and Group C, paclitaxel is diluted with saline to a given concentration, and intraperitoneally administered at 6 mg/kg body weight for a total of 3 times at intervals of 1 to 2 days. Group C was intravenously administered with compound 72 (10 mg/kg body weight) of Reference Example A dissolved in an emulsion containing soybean oil, egg-yolk lecithin, glycerol and the like immediately before intraperitoneal administration of paclitaxel (total 3 times). Thus, neither paclitaxel nor Compound 72 was administered to Group A; paclitaxel but not Compound 72 was administered to Group B; and both paclitaxel and Compound 72 were administered to Group C. Pain threshold of each group was measured 2 weeks after first paclitaxel administration. Pain threshold is a weighed value (gram) at the time when an avoidance response is observed by pressurizing the plantar part of the right hindlimb using an Electronic von Frey (IITC Life Science). The results are shown in the following Table 17. The values in the Table show mean ±standard error of the weighed values, and n is the number of the rats in each group.

TABLE 17

| | Pain threshold (g) |
|---|---|
| Group A (n = 8) | 25.8 ± 0.7 |
| Group B (n = 9) | 15.4 ± 2.6 |
| Group C (n = 8) | 24.9 ± 0.9** |

**$p < 0.001$; t-test

From the above results, compound A has been shown to have a suppressing (or mitigating) action on neurological symptoms (e.g., dysesthesia such as numbness, pain and the like) of peripheral nerve disorders induced by paclitaxel.

Experimental Example 4

Mice (C57BL/6N, male, 8-week-old) were divided into Group B and Group D. To Group B and Group D, any one of various anti-cancer agents (paclitaxel, docetaxel, vincristine, cisplatin, carboplatin, bortezomib) is diluted with saline to a given concentration, and intraperitoneally administered (paclitaxel at 10 mg/kg body weight, docetaxel at 3 mg/kg body weight, vincristine at 0.1 mg/kg body weight, cisplatin at 3 mg/kg body weight, carboplatin at 40 mg/kg body weight, bortezomib at 0.4 mg/kg body weight). Group D was intravenously administered with compound 9' (1 mg/kg body weight) of Reference Example B dissolved in solution of N methyl-D(−)-glucamine (0.01 mol/L) immediately before intraperitoneal administration of various anti-cancer agents. Pain threshold of each group was measured 3 week after the administration for paclitaxel and 1 week after the administration for the anti-cancer agents other than paclitaxel. Pain threshold is a weighed value (gram) at the time when a false escape response is observed by pressurizing the plantar part of the right hindlimb using a balance type pressing device (Ugo Basile). The results are shown in the following Table 18. The values in the Table show mean±standard error of the weighed values, and n is the number of the mice in each group.

TABLE 18

| | Pain threshold (g) |
|---|---|
| Paclitaxel administration group | |
| Group B (n = 6) | 130.0 ± 13.4 |
| Group D (n = 6) | 406.7 ± 61.2** |
| Docetaxel administration group | |
| Group B (n = 6) | 123.3 ± 8.0 |
| Group D (n = 6) | 276.7 ± 38.1** |
| Vincristine administration group | |
| Group B (n = 6) | 140.0 ± 18.6 |
| Group D (n = 6) | 306.7 ± 73.5** |

TABLE 18-continued

| | Pain threshold (g) |
|---|---|
| Cisplatin administration group | |
| Group B (n = 6) | 113.3 ± 9.9 |
| Group D (n = 6) | 193.3 ± 26.2* |
| Carboplatin administration group | |
| Group B (n = 6) | 110.0 ± 6.8 |
| Group D (n = 6) | 176.7 ± 16.7** |
| Bortezomib administration group | |
| Group B (n = 6) | 133.3 ± 12.3 |
| Group D (n = 6) | 256.7 ± 26.5** |

*$p < 0.025$, **$p < 0.001$; t-test

From the above results, compound A has been shown to have a suppressing (or mitigating) action on neurological symptoms (e.g., dysesthesia such as numbness, pain and the like) of peripheral nerve disorders induced by various anti-cancer agents.

INDUSTRIAL APPLICABILITY

The present invention is useful for suppressing (or mitigating) neurological symptoms (e.g., dysesthesia such as numbness, pain and the like) of peripheral nerve disorders which are one of the side effects caused by the administration of an anti-cancer agent. In addition, the present invention is useful for avoiding a decrease in the dosage due to the side effects of the administration of an anti-cancer agent.

This application is based on patent application No. 2010-015935 filed in Japan, the contents of which are encompassed in full herein.

The invention claimed is:

1. A method for treating a peripheral nerve disorder induced by at least one anti-cancer agent, which comprises administering ethyl (6R)-6-[N-(2-chloro-4-fluorophenyl)sulfamoyl]-1-cyclohexene-1-carboxylate or a salt thereof to a mammal in need thereof,
wherein the anti-cancer agent is selected from paclitaxel, docetaxel, vincristine, vinblastine, cisplatin, carboplatin, oxaliplatin and bortezomib, and
wherein the peripheral nerve disorder induced by the anti-cancer agent is dysesthesia.

2. The method according to claim 1, wherein the dysesthesia is numbness, pain, anesthesia and/or ache.

3. The method according to claim 1, wherein the dysesthesia is numbness and/or pain.

4. The method according to claim 1, wherein the dysesthesia is numbness.

5. The method according to claim 1, wherein the dysesthesia is pain.

6. The method according to claim 1, wherein the anti-cancer agent is paclitaxel.

7. The method according to claim 1, wherein the anti-cancer agent is oxaliplatin.

8. The method according to claim 1, wherein the anti-cancer agent is bortezomib.

9. The method according to claim 5, wherein the pain is mitigated or suppressed.

* * * * *